US012419662B2

(12) United States Patent
Thirumalai et al.

(10) Patent No.: US 12,419,662 B2
(45) Date of Patent: Sep. 23, 2025

(54) SELECTIVELY INSULATED ULTRASOUND TRANSDUCERS

(71) Applicant: Otsuka Medical Devices Co., Ltd., Tokyo (JP)

(72) Inventors: Shruthi R. Thirumalai, Fremont, CA (US); Lewis J. Thomas, III, Comitan (MX); Jaime Merino, Mountain View, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 138 days.

(21) Appl. No.: 17/457,997

(22) Filed: Dec. 7, 2021

(65) Prior Publication Data

US 2022/0265302 A1    Aug. 25, 2022

Related U.S. Application Data

(60) Provisional application No. 63/151,514, filed on Feb. 19, 2021.

(51) Int. Cl.
*A61B 17/32* (2006.01)
*A61B 17/00* (2006.01)
(Continued)

(52) U.S. Cl.
CPC ........ *A61B 17/320068* (2013.01); *A61N 7/00* (2013.01); *B06B 1/0655* (2013.01);
(Continued)

(58) Field of Classification Search
CPC .. A61B 17/320068; A61B 2017/00402; A61B 2017/00831; A61B 2017/320069;
(Continued)

(56) References Cited

U.S. PATENT DOCUMENTS

| | | | |
|---|---|---|---|
| 3,879,697 A | 4/1975 | Richard | |
| 4,549,107 A * | 10/1985 | Kaneko | G10K 11/002 310/800 |

(Continued)

FOREIGN PATENT DOCUMENTS

| | | |
|---|---|---|
| CN | 105188848 | 12/2019 |
| EP | 1579889 | 9/2005 |

(Continued)

OTHER PUBLICATIONS

International Search Report & The Written Opinion of the International Searching Authority dated Apr. 4, 2022, International Application No. PCT/IB2022/050102.

(Continued)

*Primary Examiner* — Hien N Nguyen
(74) *Attorney, Agent, or Firm* — Theresa Ann Raymer

(57) ABSTRACT

Disclosed herein are ultrasound transducers that are selectively insulated to thereby enable the transducers to be exposed to an electrically conductive fluid without causing a short circuit between electrodes of the transducers. Such a transducer includes a piezoelectric transducer body having a first surface and a second surface that are spaced apart from one another and do not intersect with one another. The ultrasound transducer also includes a first electrode disposed on the first surface, a second electrode disposed on the second surface, and an electrical insulator covering only one of first and second electrodes and configured to inhibit electrical conduction between the first electrode and the second electrode when the ultrasound transducer is placed within an electrically conductive fluid. Also disclosed are apparatuses and systems that include such a transducer. Related methods are also disclosed herein.

32 Claims, 11 Drawing Sheets

(51) Int. Cl.
*A61N 7/00* (2006.01)
*B06B 1/06* (2006.01)

(52) U.S. Cl.
CPC .............. *A61B 2017/00402* (2013.01); *A61B 2017/00831* (2013.01); *A61B 2017/320069* (2017.08); *A61N 2007/0026* (2013.01); *A61N 2007/003* (2013.01); *B06B 2201/76* (2013.01)

(58) Field of Classification Search
CPC .......... A61B 2017/00929; A61B 2017/22062; A61B 17/2202; A61B 2018/00023; A61B 2018/0022; A61N 7/00; A61N 2007/0026; A61N 2007/003; A61N 2007/0043; B06B 1/0655; B06B 2201/76; H10N 30/2027; H10N 30/883
See application file for complete search history.

(56) References Cited

U.S. PATENT DOCUMENTS

| | | |
|---|---|---|
| 4,554,925 A | 11/1985 | Young |
| 4,643,186 A | 2/1987 | Rosen |
| 4,650,466 A | 3/1987 | Luther |
| 4,709,698 A | 12/1987 | Johnston et al. |
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,295,484 A | 3/1994 | Marcus et al. |
| 5,368,591 A | 11/1994 | Lennox |
| 5,391,197 A | 2/1995 | Burdette et al. |
| 5,423,811 A | 6/1995 | Imran et al. |
| 5,558,672 A | 9/1996 | Edwards et al. |
| 5,575,788 A | 11/1996 | Baker et al. |
| 5,657,755 A | 8/1997 | Desai |
| 5,685,839 A | 11/1997 | Edwards et al. |
| 5,688,266 A | 11/1997 | Edwards et al. |
| 5,800,482 A | 9/1998 | Pomeranz et al. |
| 6,066,134 A | 5/2000 | Eggers et al. |
| 6,097,985 A | 8/2000 | Kasevich et al. |
| 6,117,101 A | 9/2000 | Diederich et al. |
| 6,254,598 B1 | 7/2001 | Edwards |
| 6,283,989 B1 | 9/2001 | Laufer et al. |
| 6,292,695 B1 | 9/2001 | Webster |
| 6,296,619 B1 | 10/2001 | Brisken et al. |
| 6,383,151 B1 | 5/2002 | Diederich et al. |
| 6,514,249 B1 | 2/2003 | Maguire et al. |
| 6,529,756 B1 | 3/2003 | Phan |
| 6,564,096 B2 | 5/2003 | Mest |
| 6,584,360 B2 | 6/2003 | Francischelli et al. |
| 6,635,054 B2 | 10/2003 | Fjield et al. |
| 6,648,883 B2 | 11/2003 | Francischelli et al. |
| 6,669,655 B1 | 12/2003 | Acker |
| 6,692,490 B1 | 2/2004 | Edwards |
| 6,719,755 B2 | 4/2004 | Sliwa, Jr. et al. |
| 6,763,722 B2 | 7/2004 | Fjield et al. |
| 6,837,886 B2 | 1/2005 | Collins |
| 6,845,267 B2 | 1/2005 | Harrison et al. |
| 6,954,977 B2 | 10/2005 | Maguire |
| 7,052,695 B2 | 5/2006 | Kalish |
| 7,156,816 B2 | 1/2007 | Schwartz et al. |
| 7,162,303 B2 | 1/2007 | Levin et al. |
| 7,371,231 B2 | 5/2008 | Rioux et al. |
| 7,510,536 B2 | 3/2009 | Foley et al. |
| 7,617,005 B2 | 11/2009 | Demarais et al. |
| 7,621,873 B2 | 11/2009 | Owen et al. |
| 7,653,438 B2 | 1/2010 | Deem et al. |
| 7,717,948 B2 | 5/2010 | Demarais et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,137,274 B2 | 3/2012 | Weng et al. |
| 8,447,414 B2 | 5/2013 | Johnson et al. |
| 8,483,831 B1 | 7/2013 | Hlavka et al. |
| 8,626,300 B2 | 1/2014 | Demarais et al. |
| 8,702,619 B2 | 4/2014 | Wang |
| 8,774,913 B2 | 7/2014 | Demarais et al. |
| 8,790,281 B2 | 7/2014 | Diederich et al. |
| 8,818,514 B2 | 8/2014 | Zarins et al. |
| 8,845,629 B2 | 9/2014 | Demarais et al. |
| 8,932,289 B2 | 1/2015 | Mayse et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 7,717,948 C1 | 8/2016 | Demarais et al. |
| 9,427,579 B2 | 8/2016 | Fain et al. |
| 9,439,598 B2 | 9/2016 | Shimada et al. |
| 9,649,064 B2 | 5/2017 | Toth et al. |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,363,359 B2 | 7/2019 | Toth et al. |
| 10,368,775 B2 | 8/2019 | Hettrick et al. |
| 10,376,310 B2 | 8/2019 | Fain et al. |
| 10,383,685 B2 | 8/2019 | Gross et al. |
| 10,398,332 B2 | 9/2019 | Min et al. |
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,850,091 B2 | 12/2020 | Zarins et al. |
| 11,801,085 B2 | 10/2023 | Wu et al. |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |

(56) References Cited

U.S. PATENT DOCUMENTS

| | | |
|---|---|---|
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0185278 A1* | 9/2004 | Sato ................. H01G 4/30 428/469 |
| 2004/0242999 A1 | 12/2004 | Vitek et al. |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2007/0060921 A1 | 3/2007 | Janssen et al. |
| 2007/0072741 A1 | 3/2007 | Robideau |
| 2007/0106292 A1 | 5/2007 | Kaplan |
| 2007/0135875 A1 | 6/2007 | Demarais et al. |
| 2008/0039746 A1 | 2/2008 | Hissong et al. |
| 2008/0215031 A1 | 9/2008 | Belfort et al. |
| 2009/0118725 A1 | 5/2009 | Auth et al. |
| 2009/0234407 A1 | 9/2009 | Hastings et al. |
| 2009/0248005 A1 | 10/2009 | Rusin et al. |
| 2011/0118723 A1 | 5/2011 | Turner et al. |
| 2011/0125206 A1 | 5/2011 | Bornzin |
| 2011/0137298 A1 | 6/2011 | Nguyen et al. |
| 2011/0208096 A1 | 8/2011 | Demarais et al. |
| 2012/0004656 A1 | 1/2012 | Jackson et al. |
| 2012/0265198 A1 | 10/2012 | Crow et al. |
| 2012/0296232 A1 | 11/2012 | Ng |
| 2013/0023897 A1 | 1/2013 | Wallace |
| 2013/0085489 A1 | 4/2013 | Fain et al. |
| 2013/0096550 A1 | 4/2013 | Hill |
| 2013/0116737 A1 | 5/2013 | Edwards et al. |
| 2013/0123770 A1 | 5/2013 | Smith |
| 2013/0131743 A1 | 5/2013 | Yamasaki et al. |
| 2013/0150749 A1 | 6/2013 | McLean et al. |
| 2013/0165925 A1 | 6/2013 | Mathur et al. |
| 2013/0274614 A1 | 10/2013 | Shimada et al. |
| 2013/0289369 A1 | 10/2013 | Margolis |
| 2013/0289682 A1 | 10/2013 | Barman et al. |
| 2014/0018788 A1 | 1/2014 | Engelman et al. |
| 2014/0058294 A1 | 2/2014 | Gross et al. |
| 2014/0257271 A1 | 9/2014 | Mayse et al. |
| 2014/0272110 A1* | 9/2014 | Taylor ................. C23C 18/1651 427/9 |
| 2014/0274614 A1 | 9/2014 | Min et al. |
| 2014/0275924 A1 | 9/2014 | Min et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0289931 A1 | 10/2015 | Puryear et al. |
| 2016/0000345 A1 | 1/2016 | Kobayashi et al. |
| 2016/0016016 A1* | 1/2016 | Taylor ............ A61B 17/320068 606/169 |
| 2016/0045121 A1 | 2/2016 | Akingba et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0134429 A1 | 5/2019 | Canney et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |
| 2020/0093505 A1 | 3/2020 | Sinelnikov et al. |
| 2020/0121961 A1 | 4/2020 | Taylor et al. |

FOREIGN PATENT DOCUMENTS

| | | |
|---|---|---|
| EP | 2359764 | 8/2011 |
| EP | 2430996 | 3/2012 |
| EP | 1503685 | 10/2012 |
| EP | 1299035 | 2/2013 |
| EP | 2842604 | 3/2015 |
| EP | 2968984 | 8/2016 |
| EP | 2995250 | 10/2019 |
| EP | 3799931 | 4/2021 |
| TW | 201946700 | 12/2019 |
| WO | WO 9902096 | 1/1999 |
| WO | WO 01/95820 | 12/2001 |
| WO | WO 02/005897 | 1/2002 |
| WO | WO 2002/019934 | 3/2002 |
| WO | WO 03/022167 | 3/2003 |
| WO | WO 03/051450 | 6/2003 |
| WO | WO 2006/041881 | 4/2006 |
| WO | WO 2006/060053 | 6/2006 |
| WO | WO 2007/014003 | 2/2007 |

OTHER PUBLICATIONS

Schmerrjr, L.W., "Nondestructive Testing," Science Direct, Encyclopedia of Vibration, [https://www.sciencedirect.com/science/article/pii/S1350417719318255], https://www.sciencedirect.com/science/article/pii/S1350417719318255, 15 pages.

Simmons, Andrew, "Ultrasound in Medical Diagnosis," Medical Physics—Ultrasound, Unit 1 Physics, Feb. 2021, 5 pages.

Office Action dated Aug. 5, 2022 in Taiwanese Patent Application No. 110148115.

Berjano, E., et al., "A Cooled Intraesophageal Balloon to Prevent Thermal Injury during Endocardial Surgical Radiofrequency Ablation of the left Atrium: a finite element study." Physics in Medicine and Biology, 50(20): 269-279, 2015.

Billard, B.E., et al., "Effects of Physical Parameters on High Temperature Ultrasound Hyperthermia," Ultrasound in Med. & Biol. vol. 16, No. 4, pp. 409-420, 1990.

Chapelon, J.Y., "Treatment of Localised Prostate Cancer with Transrectal High Intensity Focused Ultrasound," European Journal of Ultrasound 9, 31-38, 1999.

Coates, Paul et al., "Time, Temperature, Power, and Impedance Considerations for Radiofrequency Catheter Renal Denervation," Cardiovascular Revascularization Medicine 42, 171-177 (2022).

Deardorff, Dana et al., "Ultrasound Applicators with Internal Cooling for Interstitial Thermal Therapy," SPIE vol. 3594, 36-46, Jan. 1999.

Diederich, et al., "Catheter-based Ultrasound Applicators for Selective Thermal Ablation: progress towards MRI-guided applications in prostate," International Journal of Hyperthermia, 20:7, 739-756.

(56) References Cited

OTHER PUBLICATIONS

Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
European Search Report dated Nov. 19, 2018 in European Patent Application No. 218186547.
Fan, Xiaobing, et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Papadopoulos, N., "Evaluation of a Small Flat Rectangular Therapeutic Ultrasonic Transducer Intended for Intravascular Use," Ultrasonics 74, 196-203, 2017.
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Sato, Yu, et al., "Translational Value of Preclinical Models for Renal Denervation: a histological comparison of human versus porcine renal nerve anatomy," EuroIntervention, 18, e1120-e1128, 2023.
Tanaka, Kazushi et al., "A New Radiofrequency Thermal Balloon Catheter for Pulmonary Vein Isolation," Journal of the American College of Cardiology vol. 38, No. 7, 2001.
Ulmsten, Ulf et al., "The Safety and Efficacy of MenoTreat™, a new balloon device for thermal endometrial ablation," Acta Obstet Gynecol Scand 2001; 80: 52-57.
U.S. Appl. No. 60/747,137, File History.
U.S. Appl. No. 60/808,306, File History.
U.S. Appl. No. 61/405,472, File History.
Accornero, Neri et al., "Selective Activation of Peripheral Nerve Fibre Groups of Different Diameter By Triangular Shaped Stimulus Pulses", J. Physiol. (1977), 273, _ 539-560, 22 Q9S.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002, 110.
Aytac, et al., "Correlation Between the Diameter of the Main Renal Artery and the Presence of an Accessory Renal Artery", J Ultrasound Med 22:433-439, 2003 (.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99:1866-1871.
Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, 2001, May, 1041-1049 (2001).
Camasao, D.B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Charlesworth, Peter et al., Renal Artery Injury From a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Corrected Patent Owner's Response to Office Action, dated May 10, 2013, from File History of Inter Partes Reexamination U.S. Appl. No. 95/002,110.
Correspondence from PTAB Deputy Chief Clerk to Counsel re conference call request-Exhibit 3001 in the Patent Trial and Appeal Board, United States Patent and Trademark Office, Petition No. PTAB-IPR2022-00431.
Curriculum Vitae of Dr. John M. Moriarty.
Curriculum Vitae of Dr. Michael Bohm.
Curriculum Vitae of Farrell Mendelsohn.
Curriculum Vitae of Dr. Chris Daft.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.

(56) References Cited

OTHER PUBLICATIONS

Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner'sResponse, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald F. et al., "Neural Control of Renal Function", 77 Physiological Reviews No. 1, 75 (1997).
Dibona, Gerald, Sympathetic Nervous System and Kidney in Hypertension, Current Opinion in Nephrology and Hypertension, vol. 11, 197-200 (2002).
Diederich, et al., Ultrasound Catheters For Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003 ; 50(1): 41-50_doi:10.1109fTBME.2002.807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019— Preliminary Remarks for EP appeal No. T2680/16-3.3.4.01.
European Communication dated Oct. 23, 2013 in EP Application No. 12180431.4.
European Office Action re Application No. 12180431.4.
European Patent No. 12167931, Claims of the Main Request dated Sep. 30, 2016.
European Search Report (supplementary) dated Feb. 17, 2016 in European Patent Application No. 14775754.6.
European Search Report dated Mar. 1, 2021 in European Patent Application No. 20202272.9.
European Search Report for Patent Application No. EP12180431 dated Jan. 17, 2013.
Fengler, Karl et al., A Three-Arm Randomized Trial of Different Renal Denervation Devices and Techniques in Patients With Resistant Hypertension (RADIOSOUND-HTN), 139 Circulation 590 (2019).
File History to EP1802370B1 Part 1.
File History to EP1802370B1 Part 2.
File History to EP1802370B1 Part 3.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R.R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1 958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, MASSDEVICE (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).

(56) References Cited

OTHER PUBLICATIONS

Kuo, et al., "Atrial Fibrillation: New Horizons", Chang Gung Med J vol. 26 No. Oct. 10, 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., ARDIAN: Succeeding Where Drugs Fail—Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis K. et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).

Millard, et al., Renal Embolization For Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Olsson, R. et al., "A Three-Dimensional Neural Recording Microsystem With Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Osborn, J., "Catheter-Based Renal Nerve Ablation as a Novel Hypertension Therapy, Lost, and Then Found," in Translation.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to-Control or Resistant Hypertension, 2011 Int. J. Hypertension, Article 196518 (2011).

Papademetriou, et al., "Renal Sympathetic Denervation: Hibernation or Resurrection?", Cardiology 2016 ; 135, 11 pgs.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

(56) References Cited

OTHER PUBLICATIONS

Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Romanes, G.J., Cunningham's Textbook of Anatomy (11th ed. 1972).
Ryan, Thomas et al., Proceedings of Thermal Treatment of Tissue with Image Guidance, Progress in Biomedical Optics, vol. 3594 (1999).
Ryan, Thomas P._ Thermal Treatment of Tissue with Image Guidance; Ultrasound Catheters For Circumferential Cardiac Ablation 1999.
Ryan, Steve, What are the Risks Associated with a Pulmonary Vein Ablation Procedure?, Atrial Fibrillation: Resources for Patients (last accessed Oct. 18, 2022).
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP.2010.5495604.
Sanchez-Quintana, Damian et al., How close are the phrenic nerves to cardiac structures? Implications for cardiac interventionalists, 16 J. Cardiovasc. Electrophysiol 309 (2005) ("Sánchez-Quintana").
Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH.0b013e328344db3a.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Shimizu, Kazumasa et al., Sympathetic Dysfunction in Heart Failure, Bailliere's Clinical Endocrinology and Metabolism, vol. 7, No., 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015 ; 9(10): 794-801 . doi:10.1016/j.jash.2015.07.012.

(56) References Cited

OTHER PUBLICATIONS

Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." PACE, 21 :2517- 2521 (1998).
Vaezy, Shahram et al., Image-Guided Acoustic Therapy, Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt-Sensitive Rabbits with Genetic Baroreflex Impairment", 90 Clinical Science 287 (1996).
Xu, J. et al., "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021.
U.S. Appl. No. 10/408,665.
U.S. Appl. No. 60/624,793.
U.S. Appl. No. 60/370,190.
U.S. Appl. No. 60/415,575.
U.S. Appl. No. 60/442,970.
U.S. Appl. No. 60/616,254.
U.S. Appl. No. 60/816,999.
U.S. Appl. No. 14/683,966, Non Final Office Action mailed Jun. 12, 2017, 14 pgs.
U.S. Appl. No. 14/683,966, Response filed Nov. 10, 2017 to Non Final Office Action mailed Jun. 12, 2017, 13 pqs.
U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.
U.S. Appl. No. 15/204,349, Preliminary Amendment filed Nov. 30, 2016, 3 pgs.
U.S. Appl. No. 15/204,349, Restriction Requirement mailed May 17, 2018, 7 pgs.
U.S. Appl. No. 15/204,349, Response filed Jun. 5, 2018 to Restriction Requirement mailed May 17, 2018, 7 pgs.
U.S. Appl. No. 15/204,349, Non Final Office Action mailed Nov. 27, 2018, 14 pgs.
U.S. Appl. No. 15/204,349, Response filed Feb. 27, 2019 to Non Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non Final Office Action mailed Nov. 27, 2018, 15 pgs.
U.S. Appl. No. 15/299,694, Response filed Feb. 27, 2019 to Non-Final Office Action mailed Nov. 27, 2018 , 10 pgs.
U.S. Appl. No. 15/299,694, Final Office Action mailed Apr. 22, 2019, 16 pgs.
U.S. Appl. No. 15/299,694, Response filed Jun. 24, 2019 to Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.
U.S. Appl. No. 15/943,354, Response filed Dec. 19, 2019 to Restriction Requirement mailed Nov. 20, 2019, 8 pages.
U.S. Appl. No. 15/943,354, Non Final Office Action mailed Jan. 13, 2020, 6 pages.
U.S. Appl. No. 15/943,354, Non Final Office Action mailed Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Non Final Office Action mailed Jun. 11, 2020, 8 pages.
U.S. Appl. No. 16/517,180, Preliminary Amendment filed Jul. 19, 2019, 12 pgs.
File History of U.S. Appl. No. 12/754,337.
File History to U.S. Pat. No. 9,943,666.
File History to U.S. Pat. No. 9,981,108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.

(56) References Cited

OTHER PUBLICATIONS

Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Borchert, Bianca et al., "Lethal Atrioesophageal Fistula After Pulmonary Vein Isolation using High-Intensity Focused Ultrasound (HIFU)" J. Hrthm vol. 5, Issue 1, p. 145-148, Jan. 2008.
Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59-62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (SPYRAL HTN OFF-MED) and presence (SPYRAL HTN ON-MED) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, P.R. et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A κ-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.
Applications, Second Edition, Edited by Shoei K. Stephen Huang, MD & David J. Wilber, MD, pp. 103-112, 2000.
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessary pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.

(56) References Cited

OTHER PUBLICATIONS

Häcker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol., vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.
Lele, P.P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue Volumes Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.

Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.
Tellez, Armando et al., "Renal Artery Nerve Distribution and Density in the Porcine Model: Biologic Implications for the Development of Radiofrequency Ablation Therapies," Translational Research vol. 162 No.6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Trippodo, Nick C. et al., "Similarities of Genetic (Spontaneous) Hypertension," Circulation Research vol. 48, No. 3, p. 309-319, Mar. 1981.
Urban, Bruce A. et al., "Three-dimensional Volume-rendered CT Angiography of the Renal Arteries and Veins: Normal Anatomy, Variants, and Clinical Applications," RG vol. 21 No. 2, p. 373-386, Mar.-Apr. 2001.
Wang, Shyh-Hau et al., "Effects of Low Intensity Ultrasound on the Conduction Property of Neural Tissues," IEEE International Ultrasonics, Ferroelectrics, and Frequency Control Joint $50^{th}$ Anniversary Conference, p. 1824-1827, 2004.
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, pg. III-08-III-115, Sep.-Oct. 1982.
Wulff, V.J. et al., "Effects of Ultrasonic Vibrations on Nerve Tissues," p. S.E.B.M., vol. 76, p. 361-366, 1951.
Yarmolenko, Pavel S. et al., "Thresholds for thermal damage to normal tissues: An update," Int. J. Hyperthermia, vol. 27 No.4, p. 320-343, Jun. 2011.
Young, Robert R. et al., "Functional Effects of Focused Ultrasound on Mammalian Nerves," Science, vol. 134, p. 1521-1522, Nov. 1961.
Zimmer, J.E. et al., "The Feasibility of Using Ultrasound for Cardiac Ablation," IEEE Transactions on Biomedical Engineering, vol. 42, No. 9, p. 891-897, Sep. 1995.

* cited by examiner

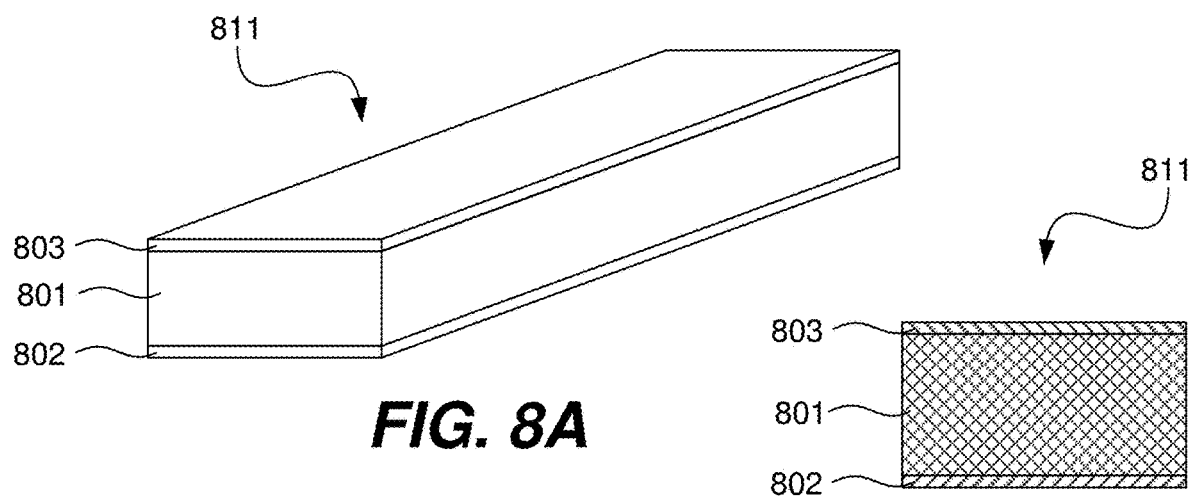
FIG. 8A
FIG. 8B
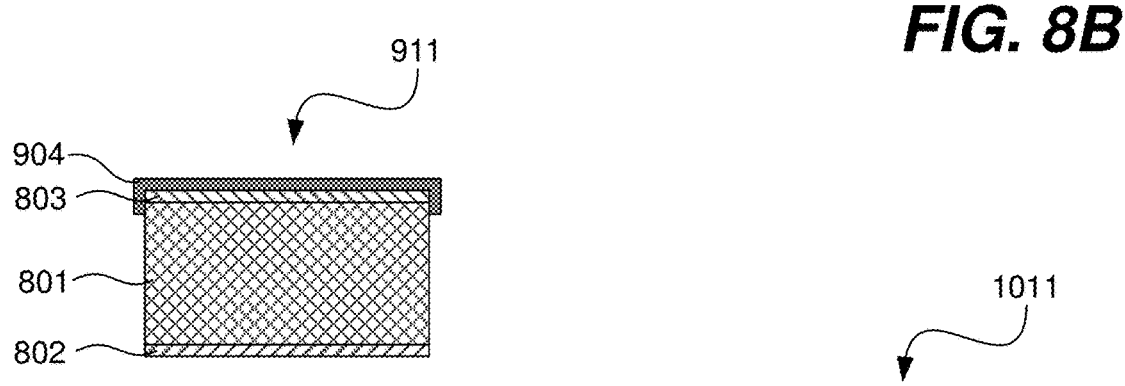
FIG. 9
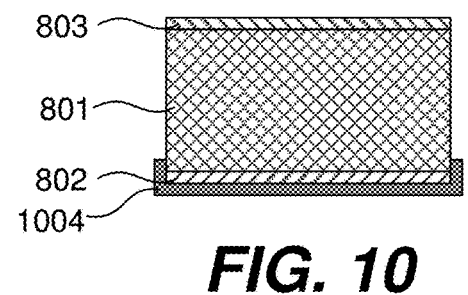
FIG. 10

SELECTIVELY INSULATED ULTRASOUND TRANSDUCERS

CLAIM OF PRIORITY

This application claims priority to U.S. Provisional Patent Application No. 63/151,514, titled "SELECTIVELY INSULATED ULTRASOUND TRANSDUCERS," by Thirumalai et al., filed Feb. 19, 2021, which incorporated by reference herein in its entirety.

FIELD OF THE TECHNOLOGY

This application relates generally to minimally-invasive apparatuses, systems and methods that provide energy delivery to a targeted anatomical location of a subject, and more specifically, to catheter-based, intraluminal apparatuses, systems and methods including or utilizing an ultrasound transducer configured to emit ultrasonic energy for the treatment of tissue, such as nerve tissue.

BACKGROUND

According to the Centers for Disease Control and Prevention (CDC), about 1 in every 3 adults suffer from high blood pressure, also known as hypertension. Left untreated, hypertension can result in renal disease, arrhythmias and heart failure. In recent years, the treatment of hypertension has focused on interventional approaches to inactivate the renal nerves surrounding the renal artery. Autonomic nerves tend to follow blood vessels to the organs that they enervate. Catheters may reach specific structure that may be proximate to the lumens in which they travel. For example, one system employs a radio frequency (RF) generator connected to a catheter having multiple electrodes placed against the intima of the renal artery and used to create an electrical field in the vessel wall and surrounding tissue that results in resistive (ohmic) heating of the tissue to a temperature sufficient to ablate the tissue and the renal nerve passing through that tissue. To treat all the renal nerves surrounding the renal arteries, the RF electrodes are repositioned several times around the inside of the renal artery. However, the relatively confined electric fields created by the RF electrodes may miss some of the renal nerves, leading to an incomplete treatment. Additionally, to heat the renal nerves, the RF electrodes must contact the intima, posing a risk of damage or necrosis to the intima, which in turn can lead to thrombus formation, fibrosis of the vessel wall, mechanical weakening of the vessel and possible vessel dissection.

Another approach to renal nerve deactivation is the use of high-intensity focused ultrasound (HIFU), which relies on vibrational energy to cause frictional heating and disruption of the tissue, and in turn, raise the tissue temperature sufficiently to cause ablation or remodeling. However, the use of HIFU intravascularly may result in, at most, the formation of a thin focal ring in the vessel and surrounding tissue. If applied to renal denervation, it would be difficult to align this thin ring with the renal nerves because the renal nerves lie at differing radial distances along the length of the renal arteries. Also problematic is that the thin focal ring results in a small longitudinal treatment zone relative to the axis of the vessel.

U.S. Pat. Nos. 9,943,666, 9,981,108, and 10,039,901 to Warnking, U.S. Pat. Nos. 9,700,372, 9,707,034, and 10,368,944 to Schaer, and U.S. Pat. Nos. 10,350,440 and 10,456,605 to Taylor, the entire contents of each which is incorporated by reference herein, solve many of the drawbacks of RF and HIFU systems such as described above. An example embodiment of the system includes an ultrasound transducer positioned along a distal end of a catheter designed to be inserted into a blood vessel (e.g., the renal artery). The ultrasound transducer emits one or more therapeutic doses of unfocused ultrasound energy, which heats the tissue adjacent to the body lumen within which the transducer is disposed. Such unfocused ultrasound energy may, for example, ablate target nerves surrounding that body lumen, but without damaging non-target tissue such as the inner lining of the body lumen or unintended organs outside of the body lumen. The system may include a balloon mounted at the distal end of the catheter that is designed to cool the blood vessel when a cooling fluid is delivered to the balloon. Such a design enables creation of one or more ablation zones sufficient to achieve long-term nerve inactivation at different locations around the circumference of the blood vessel.

The ultrasound transducer may include first and second electrodes which are arranged on either side of a cylindrical piezoelectric material, such as lead zirconate titanate (PZT). To energize the transducer, a voltage is applied across the first and second electrodes at frequencies selected to cause the piezoelectric material to resonate, thereby generating vibration energy that is emitted radially outward from the transducer. The transducer is designed to provide a generally uniform and predictable emission profile, to inhibit damage to surrounding non-target tissue. In addition, a cooling fluid is circulated through the balloon, both prior to, during, and after activation of the transducer, so as to reduce heating of an inner lining of the body lumen. In this manner, the peak temperatures achieved by tissue within the cooling zone remain lower than for tissue located outside the cooling zone.

It is desirable to inhibit electrical shorts that may occur between an ultrasound transducer's electrodes via a fluid. One way of inhibiting such electrical shorts is to use a non-electrically conductive cooling fluid within the balloon, such as deionized water having a sufficiently low electrical conductivity. However, it would be desirable to have more flexibility in selection of the type of cooling fluid that is used within a balloon. Additionally, it may be desirable to use an ultrasound transducer without a balloon, in which case the ultrasound transducer may be inserted directly into a body lumen through which electrically conductive blood flows. In such a procedure, it would be desirable to inhibit electrical shorts between the ultrasound transducer's electrodes via the electrically conductive blood.

SUMMARY

Disclosed herein are various ultrasound transducers, wherein only one of the electrodes of such a transducer is covered by an electrical insulator to inhibit electrical shorts between the ultrasound transducer's electrodes via an electrically conductive fluid, which, for instance, may be a cooling fluid within a balloon, or may be blood where the transducer is inserted directly into a body lumen through which electrically conductive blood flows. Such ultrasound transducers may be referred to herein as selectively insulated transducers or partially insulated transducers, or more succinctly as transducers. Ultrasound-based tissue treatment apparatuses and systems having selectively insulated transducers are also disclosed herein. The systems are catheter-based and may be delivered intraluminally (e.g., intravascularly) so as to place the selectively insulated transducer within a suitable body lumen such as a blood vessel, e.g., the renal artery. The selectively insulated transducer may be activated to deliver unfocused ultrasonic energy radially outwardly so as to neuromodulate tissue within the target anatomical region, and thus treat a condition, e.g., hypertension. In addition, the selectively insulated transducer may be disposed within a balloon that is filled with a cooling fluid before and during treatment. The cooling fluid may act to transfer heat away from the ultrasound transducer and surrounding tissue during use. In such embodiments, the cooling fluid may be electrically conductive.

In accordance with certain embodiments of the present technology, an ultrasound transducer includes a piezoelectric transducer body having a first surface and a second surface that are spaced apart from one another and do not intersect with one another. The ultrasound transducer also includes first electrode disposed on the first surface, a second electrode disposed on the second surface, and an electrical insulator directly or indirectly covering the first electrode. The second electrode is not covered by an electrical insulator and is thereby configured to come into contact with an electrically conductive fluid when the ultrasound is placed within the electrically conductive fluid.

In accordance with certain embodiments of the present technology, the electrical insulator covers the first electrode and is configured to inhibit the first electrode from coming into contact with an electrically conductive fluid when the ultrasound transducer is placed within the electrically conductive fluid, and thereby inhibit electrical conduction between the first electrode and the second electrode when the ultrasound transducer is placed within the electrically conductive fluid. In such embodiments, the second electrode is not covered by an electrical insulator. Because the second electrode is not covered by an electrical insulator, the second electrode will come into contact with the electrically conductive fluid when the ultrasound transducer is placed within the electrically conductive fluid.

In accordance with certain embodiments of the present technology, the piezoelectric transducer body is configured to generate ultrasonic waves in response to a voltage being applied between the first and second electrodes, which can also be referred to as application of a voltage between the first and second electrodes. In such embodiments, the electrical insulator that covers the first electrode is configured to inhibit, and preferably prevent, a short circuit from occurring between the first electrode and the second electrode when the ultrasound transducer is placed within the electrically conductive fluid and the voltage is applied between the first and second electrodes.

In accordance with certain embodiments of the present technology, the piezoelectric transducer body comprises a hollow tube of piezoelectric material having an inner surface and an outer surface, the inner surface being one of the first and second surfaces of the piezoelectric transducer body, and the outer surface being the other one of the first and second surfaces of the piezoelectric transducer body. In certain such embodiments, the first electrode is disposed on one of the inner and outer surfaces of the hollow tube of piezoelectric material, and the second electrode is disposed on the other one of the inner and outer surfaces of the hollow tube of piezoelectric material. In accordance with certain embodiments of the present technology, the hollow tube of piezoelectric material is cylindrically shaped, such that it has a circular shaped radial cross-section. In alternative particular embodiments, the hollow tube of piezoelectric material can have other shapes besides being cylindrical with a circular cross-section. Other cross-sectional shapes for the hollow tube of piezoelectric material, and more generally the piezoelectric transducer body, include, but are not limited to, an oval or elliptical cross-section, a square or rectangular cross-section, pentagonal cross-section, a hexagonal cross-section, a heptagonal cross-section, an octagonal cross-section, and/or the like. In still other embodiments, the piezoelectric transducer body is not hollow, e.g., the piezoelectric transducer body can have a generally solid rectangular shape, or some other solid shape. For instance, the piezoelectric transducer body could be a solid piezoelectric transducer body.

In accordance with certain embodiments of the present technology, the piezoelectric transducer body is configured to deliver acoustic energy in a frequency range of 8.5 to 9.5 MHz. In accordance with certain embodiments of the present technology, the piezoelectric transducer body is configured to produce an acoustic output power within a range of 5 to 45 Watts in response to an input electrical power within a range of 10 to 80 Watts.

In accordance with certain embodiments of the present technology, the electrical insulator that covers the first electrode inhibits (and preferably prevents) the first electrode from coming into contact with the electrically conductive fluid when the ultrasound transducer is positioned in the electrically conductive fluid. In such embodiments, an electrical insulator does not cover the second electrode, and thus, the second electrode will come into contact with the electrically conductive fluid when the ultrasound transducer is positioned in the electrically conductive fluid. In other words, only one of the first and second electrodes is covered by an electrical insulator.

In an embodiment, the electrically conductive fluid comprises one of blood, saline, non-pure water, or sodium lactate solution. Hence, in this embodiment, the electrically conductive fluid is selected from the group that consists of blood, saline, non-pure water, sodium lactate solution, and a combination thereof.

In an embodiment, the first electrode comprises a major peripheral surface and longitudinal ends. In such an embodiment, a portion of the electrical insulator covers the major peripheral surface of the first electrode and is made of a first type of electrically insulating material. In this embodiment, a further or remaining portion of the electrical insulator covers the longitudinal ends of the first electrode and is made of the first type of electrically insulating material or a second, different type of electrically insulating material.

In accordance with certain embodiments of the present technology, the ultrasound transducer is configured to be placed within a balloon that is at least partially filled with the electrically conductive fluid that is used to cool a portion of a body lumen within which the ultrasound transducer may be positioned. The cooling fluid can also be used to cool the transducer that is positioned with the balloon. In certain such embodiments, the electrically conductive fluid, that the balloon is at least partially filled with, comprises at least one of saline, non-pure water, or sodium lactate solution. Hence, in such an embodiment, the electrically conductive fluid is selected from the group consisting of saline, non-pure water, sodium lactate solution and a combination thereof. The use of other electrically conductive fluids are also possible and within the scope of the embodiments described herein.

In accordance with certain embodiments of the present technology, which may be referred to as balloonless embodiments, the ultrasound transducer is configured to be directly exposed to blood flowing through a body lumen within which the ultrasound transducer may be positioned. In such embodiments, the electrically conductive fluid comprises or is the blood.

In accordance with certain embodiments of the present technology, the electrical insulator comprises parylene. Alternative or additional materials can be used to provide the electrical insulator, such as, but not limited to, cyanoacetate, epoxy resin, nylon, polytetrafluoroethylene (PTFE), polyimide, polyethylene, polyethylene terephthalate, polyvinyl chloride (PVC), and synthetic diamond coating, or combinations thereof. For instance, in an embodiment, the electrical insulator comprises parylene disposed on and covering an outer circumference of the first electrode and an epoxy resin disposed on and covering longitudinal ends of the first electrode. In another embodiment, the electrical insulator consists of parylene.

In an embodiment, the ultrasound transducer further comprises a cable contacting the first electrode and configured to provide power to the first electrode. In this embodiment, the electrical insulator covers both a peripheral surface of the first electrode and a contact between the cable and the first electrode.

In a particular embodiment, the electrical insulator comprises a first insulator disposed on the first electrode and a second insulator disposed on the contact, which is a same as or different than the first insulator.

The above described embodiments of the ultrasound transducer may be combined.

Certain embodiments of the present technology are directed to an apparatus comprising a balloon configured to receive a cooling fluid, and an ultrasound transducer disposed within the balloon. In certain such embodiments, the ultrasound transducer comprises a hollow tube of piezoelectric material having an inner surface and an outer surface. A first electrode is disposed on one of the inner and outer surfaces of the hollow tube of piezoelectric material. A second electrode is disposed on the other one of the inner and outer surfaces of the hollow tube of piezoelectric material. An electrical insulator covers the first electrode and is configured to inhibit the first electrode from coming into contact with the cooling fluid received by the balloon. Hence, in this embodiment, the electrical insulator is configured to inhibit electrical conduction between the first electrode and the second electrode.

In an embodiment, the hollow tube of piezoelectric material is cylindrical hollow tube of piezoelectric material.

In an embodiment, the electrically conductive cooling fluid can comprise at least one of saline, non-pure water, or sodium lactate solution, but is not limited thereto. Hence, in an embodiment, the electrically conductive cooling fluid is selected from the group consisting of saline, non-pure water, sodium lactate solution and a combination thereof.

In certain embodiments, the first electrode (which is covered by the electrical insulator) is disposed on the outer surface of the hollow tube of piezoelectric material. In other embodiments, the first electrode (which is covered by the electrical insulator) is disposed on the inner surface of the hollow tube of piezoelectric material. The certain such embodiments, second electrode is not covered by an electrical insulator, and thus, comes into contact with the cooling fluid received by the balloon.

In accordance with certain embodiments of the present technology, the apparatus further comprises a controller configured to apply a voltage between the first and second electrodes to thereby cause the ultrasound transducer to generate ultrasonic waves. In such embodiments, the electrical insulator inhibits (and preferably prevents) a short circuit from occurring between the first electrode and the second electrode when the cooling fluid received within the balloon is an electrically conductive cooling fluid and the voltage is applied between the first and second electrodes by the controller. In some such embodiments, the first electrode is the outer electrode. In other embodiments, the first electrode is the inner electrode.

In an embodiment, the electrical insulator comprises one or more of the following parylene, cyanoacetate, epoxy resin, nylon, polytetrafluoroethylene (PTFE), polyimide, polyethylene, polyethylene terephthalate, polyvinyl chloride (PVC) and synthetic diamond coating.

In accordance with certain embodiments of the present technology, a method comprises providing an ultrasound transducer having a first surface and a second surface that are spaced apart from one another and do not intersect with one another, wherein a first electrode is disposed on the first surface, and a second electrode disposed on the second surface. The method also comprises covering only one of the first and second electrodes with an electrical insulator, and exposing the ultrasound transducer to an electrically conductive fluid that comes into contact with the second electrode, and that is inhibited from coming into contact with the first electrode by the insulator that covers the first electrode. Additionally, while the ultrasound transducer is exposed to the electrically conductive fluid, the method includes applying a voltage between the first and second electrodes to thereby cause the ultrasound transducer to produce ultrasonic waves. The method further comprises, utilizing the electrical insulator, inhibiting a short circuit from occurring between the first electrode and the second electrode, while the ultrasound transducer is exposed to the electrically conductive fluid and the voltage is applied between the first and second electrodes. The aforementioned electrically conductive fluid can comprise at least one of saline, non-pure water, or sodium lactate solution, but is not limited thereto. The aforementioned electrically conductive fluid can alternatively be blood that is flowing through a body lumen.

In accordance with certain embodiments, the method further comprises placing the ultrasound transducer inside of a balloon. In such embodiments, the step of exposing the ultrasound transducer to the electrically conductive fluid comprises at least partially filling the balloon with the electrically conductive fluid. Such a method can also include inserting the balloon, with the ultrasound transducer therein, into a body lumen. In such embodiments, the step of applying the voltage between the first and second electrodes, to thereby cause the ultrasound transducer to produce ultrasonic waves, occurs while the balloon is within the body lumen.

In accordance with alternative embodiments, which can be referred to as balloonless embodiments, the method further comprises inserting the ultrasound transducer into a body lumen through which blood is flowing such that the ultrasound transducer comes into contact with the blood. In such embodiments, the electrically conductive fluid comprises the blood, and the step of exposing the ultrasound transducer to the electrically conductive fluid comprises exposing the ultrasound transducer to the blood.

In accordance with certain principles of the present technology, an electrically conductive cooling fluid, e.g., saline or sodium lactate solution, may be used with the selectively insulated transducer. Saline and sodium lactate solution are readily available throughout hospitals and other treatments centers, and thus may enhance ease of integrating the present systems into surgical settings. Accordingly, the selectively insulated transducer may include an electrical insulator that covers one of an inner electrode or an outer electrode of the insulated transducer, which inhibits shorting between the transducer's electrodes via an electrically conductive fluid that is within the balloon. Specifically, in the absence of the electrical insulator, if the balloon is filled with an electrically conductive fluid, then applying a voltage across the inner and outer electrodes may cause an electrical short that inhibits the ultrasound material of the transducer from generating ultrasonic waves of a desired output power.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIG. 3A1 illustrates a cross-sectional view of a catheter shaft, along the line A-A in FIG. 2C, in accordance with an embodiment.

FIG. 3A2 illustrates a cross-sectional view of the catheter shaft, along the line A-A in FIG. 2C, in accordance with an alternative embodiment.

FIG. 8A illustrates a perspective view of an alternative configuration of piezoelectric transducer, wherein the transducer body is rectangular and the electrodes of the transducer are planar.

FIG. 8B illustrates a cross-sectional view of the piezoelectric transducer introduced in FIG. 8A.

FIG. 9 illustrates a cross-sectional view of a selectively insulated transducer according to another embodiment of the present technology.

FIG. 10 illustrates a cross-section view of a selectively insulated transducer according to a further embodiment of the present technology.

DETAILED DESCRIPTION

Acoustic-based tissue treatment transducers, apparatuses, systems are provided herein. Preferably, the systems are catheter-based and may be delivered intraluminally (e.g., intravascularly) so as to place a transducer within a target anatomical region of the subject, for example, within a suitable body lumen such as a blood vessel. Once properly positioned within the target anatomical region, the transducer can be activated to deliver unfocused ultrasonic energy radially outwardly so as to suitably heat, and thus treat, tissue within the target anatomical region. The transducer can be activated at a frequency, time, and energy level suitable for treating the targeted tissue. In one nonlimiting example, the unfocused ultrasonic energy generated by the transducer may target select nerve tissue of the subject, and may heat such tissue in such a manner as to neuromodulate (e.g., fully or partially ablate, necrose, or stimulate) the nerve tissue. In a manner such as described in the Warnking, Schaer, and Taylor patents mentioned above, neuromodulating renal nerves may be used to treat various conditions, e.g., hypertension, chronic kidney disease, atrial fibrillation, arrhythmia, heart failure, chronic kidney disease, end stage renal disease, myocardial infarction, anxiety, contrast nephropathy, diabetes, metabolic disorder and insulin resistance, etc. However, it should be appreciated that the transducers suitably may be used to treat other nerves and conditions, e.g., sympathetic nerves of the hepatic plexus within a hepatic artery responsible for blood glucose levels important to treating diabetes, or any suitable tissue, e.g., heart tissue triggering an abnormal heart rhythm, and is not limited to use in treating (e.g., neuromodulating) renal nerve tissue.

In intraluminal systems, ultrasound transducers may be disposed within balloons that are filled with a cooling fluid before and during treatment. Alternatively, an ultrasound transducer may be exposed directly to the bloodstream, without a surrounding balloon, in what may be referred to as balloonless embodiments.

Overview of System Components and Features

Figure 1:
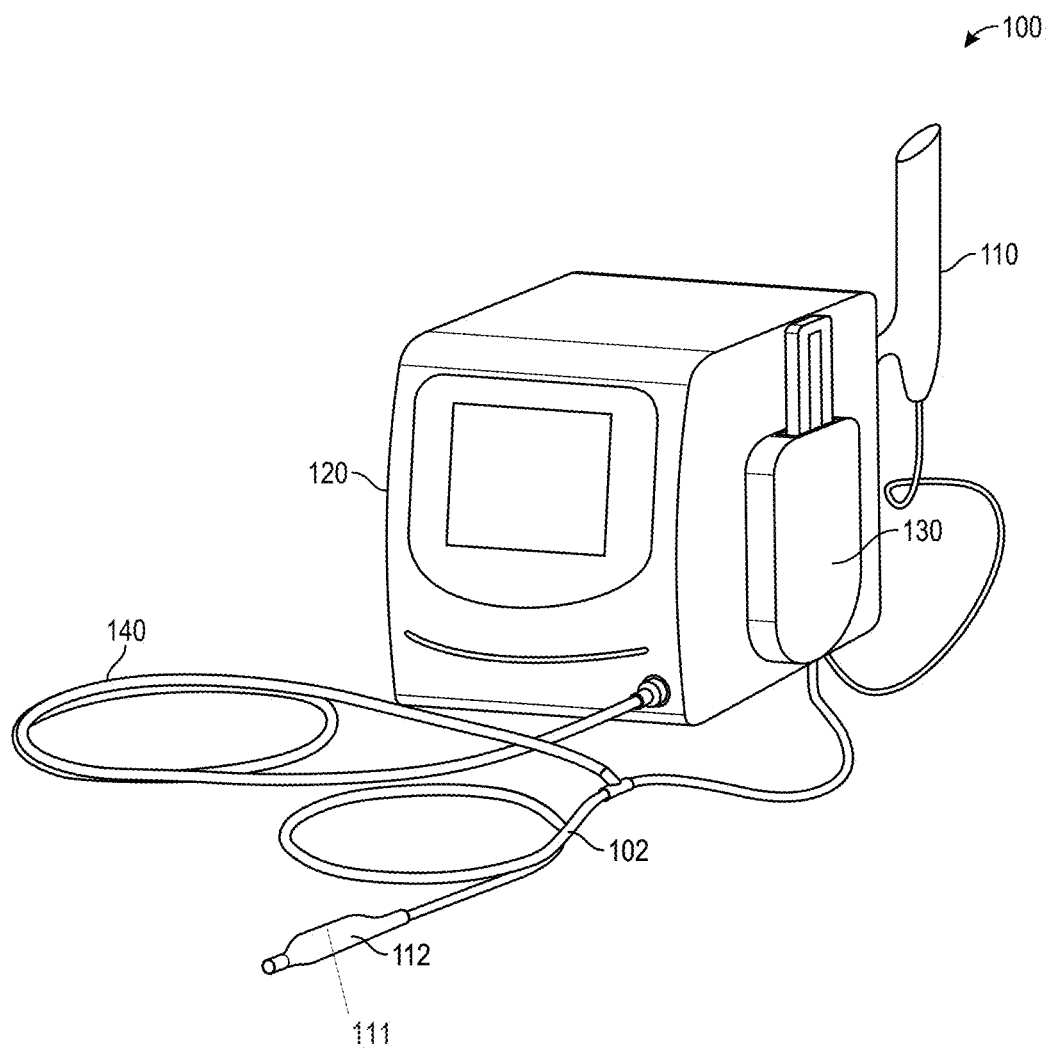
FIG. 1 illustrates selected components of an ultrasound-based tissue treatment system in accordance with certain embodiments of the present technology.
Figure 2A:
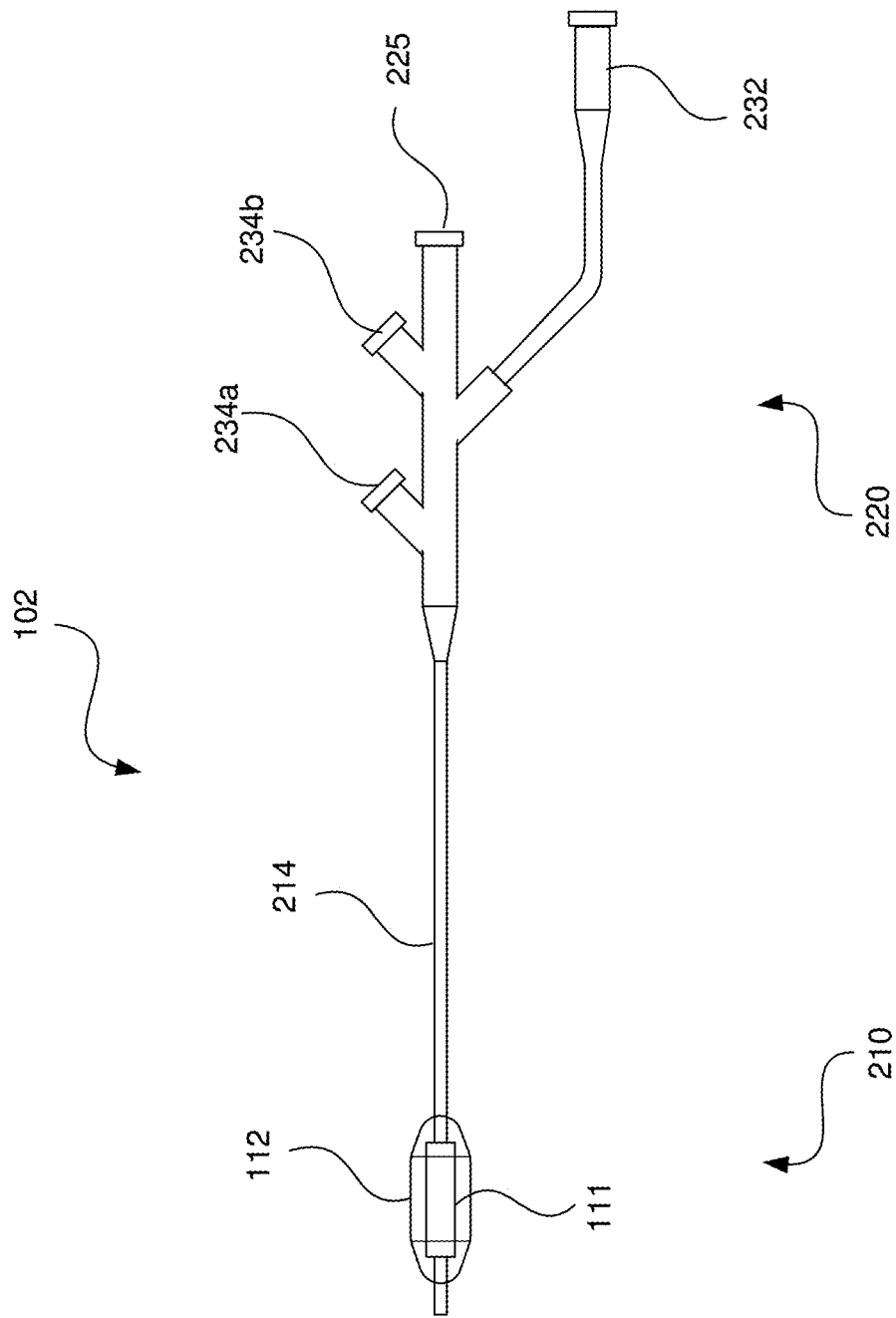
FIG. 2A illustrates a side view of selected components of the ultrasound-based tissue treatment system introduced in FIG. 1.
Figure 2B:
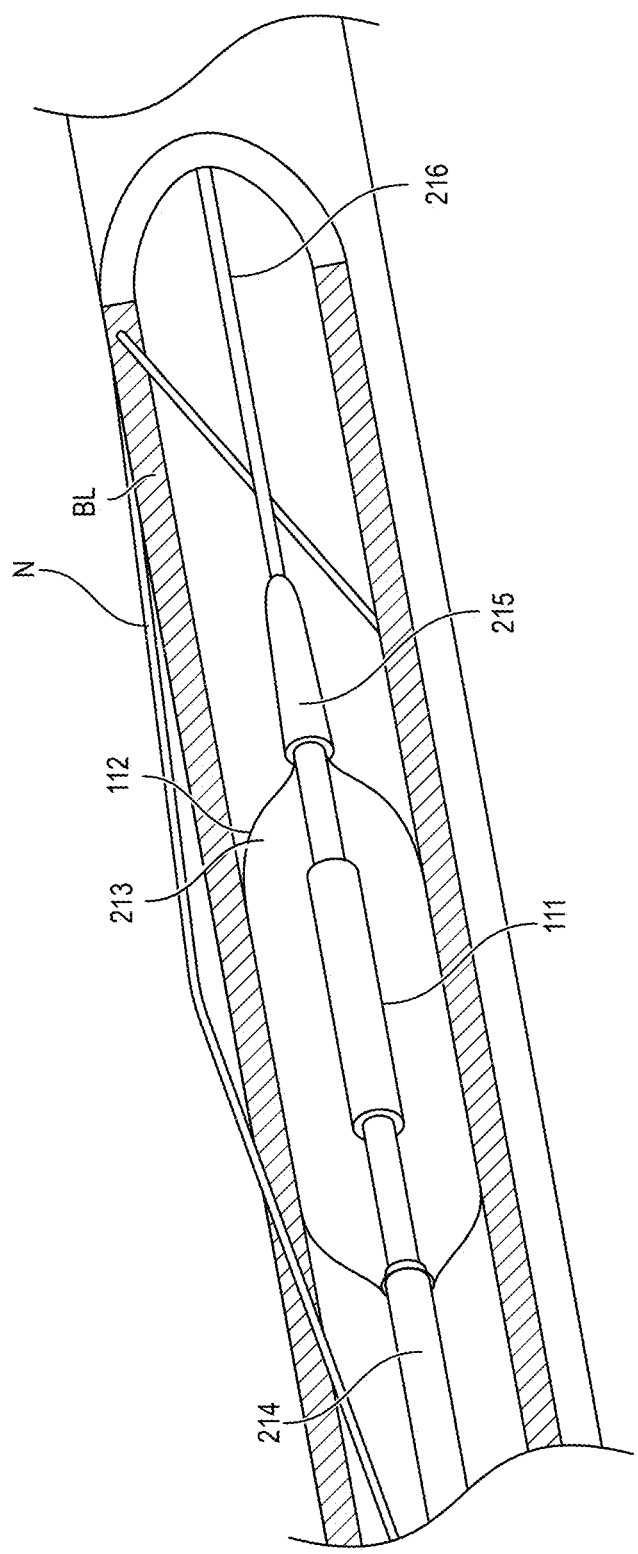
FIG. 2B illustrates a perspective view of additional selected components of the ultrasound-based tissue treatment system inserted into a body lumen in according to various configurations provided herein.

FIGS. 1, 2A, and 2B illustrate features of an ultrasound-based tissue treatment system 100, according to various configurations provided herein. Referring initially to FIG. 1, the system 100 is shown as including a catheter 102, a controller 120, and a connection cable 140. In certain embodiments, the system 100 further includes an ultrasound transducer 111 within a balloon 112, a reservoir 110, a cartridge 130, and a control mechanism, such as a handheld remote control. In certain embodiments, which can be referred to as "balloonless" embodiments, the system 100 does not include the balloon 112. In certain such balloonless embodiments, the system 100 also does not include the reservoir 110 and the cartridge 130. In certain other balloonless embodiments, the system 100 does include the reservoir 110 and/or the cartridge 130.

In the embodiment shown in FIG. 1, the controller 120 is shown as being connected to the catheter 102 through the cartridge 130 and the connection cable 140. In certain embodiments, the controller 120 interfaces with the cartridge 130 to provide a cooling fluid to the catheter 102 for selectively inflating and deflating the balloon 112. The balloon 112 can be made, e.g., from nylon, a polyimide film, a thermoplastic elastomer (such as those marked under the trademark PEBAX™), a medical-grade thermoplastic polyurethane elastomers (such as those marketed under the trademark PELLETHANE™), pellethane, isothane, or other suitable polymers or any combination thereof, but is not limited thereto.

Referring now to FIG. 2A, the catheter 102 includes a distal portion 210 and a proximal portion 220. The catheter 102 includes a catheter shaft 214, which can include one or more lumens extending therethrough. For an example, the catheter shaft 214 includes a guidewire lumen 225 that is shaped, sized and otherwise configured to receive a guidewire. In certain embodiments suitable, e.g., for renal denervation, the catheter 102 may be about 6 French in diameter and about 85 cm in length. The proximal portion 220 of the catheter 102 may include one or more connectors or couplings. For example, the proximal portion 220 may include one or more electrical coupling(s) 232. The catheter 102 may be coupled to the controller 120 by connecting the electrical coupling(s) 232 to the connection cable 140. The connection cable 140 may be removably connected to the controller 120 and/or the catheter 102 via a port on the controller 120 and/or the catheter 102, in order to permit use of multiple catheters during a procedure. In certain embodiments, e.g., where only one catheter 102 needs to be used during a procedure, the connection cable 140 may be permanently connected to the controller 120.

In certain embodiments, the proximal portion 220 of the catheter 102 may further include one or more fluidic ports, e.g., a fluidic inlet port 234a and a fluidic outlet port 234b, via which an expandable member (e.g., balloon 112) may be fluidly coupled to the reservoir 110 (shown in FIG. 1), which supplies cooling fluid. The reservoir 110 optionally may be included within controller 120, attached to the outer housing of controller 120 as shown in FIG. 1, or may be provided separately. In other embodiments, the fluidic inlet port 234a and the fluidic outlet port 234b, the balloon 112, and the reservoir 110 may all be absent from the system 100. Other variations are also possible and within the scope of the embodiments described herein.

FIG. 2B illustrates a perspective view of selected components of the catheter 102, e.g., components of the distal portion 210 as may be inserted into a body lumen BL of a subject. In FIG. 2B, the body lumen BL is a blood vessel (e.g., a renal artery) that has a plurality of nerves N in an outer layer (e.g., adventitia layer) of the blood vessel. As illustrated in FIG. 2B, the distal portion 210 may include the ultrasound transducer 111, the balloon 112 filled with a cooling fluid 213, the catheter shaft 214, and/or a guidewire support tip 215 configured to receive a guidewire 216.

The transducer 111 may be disposed partially or completely within the balloon 112, which may be inflated with a cooling fluid 213 so as to contact the interior surface (e.g., intima) of the body lumen BL. In certain embodiments, the transducer 111 may be used to output an acoustic signal when the balloon 112 fully occludes a body lumen BL. The balloon 112 may center the transducer 111 within the body lumen BL. In certain embodiments, e.g., suitable for renal denervation, the balloon 112 is inflated while inserted in the body lumen BL of the patient during a procedure at a working pressure of about 1.4 to 2 atm using the cooling fluid 213. The balloon 112 may be or include a compliant, semi-compliant or non-compliant medical balloon. The balloon 112 is sized for insertion in the body lumen BL and, in the case of insertion into the renal artery, for example, the balloon 112 may be selected from available sizes including outer diameters of 3.5, 4.2, 5, 6, 7, or 8 mm, but not limited thereto. In some embodiments, as shown in FIG. 2B, when inflated by being filled with the cooling fluid 213 under the control of the controller 120, the outer wall of the balloon 112 may be generally parallel with the outer surface of the transducer 111. Optionally, the balloon 112 may be inflated sufficiently as to be in apposition with the body lumen BL. For example, when inflated, the balloon 112 may at least partially contact, and thus be in apposition with, the inner wall of the body lumen BL. In other configurations, the balloon 112 is configured not to contact the body lumen BL when expanded. Additionally, or alternatively, the balloon 112 may be maintained at a specified size by pushing cooling fluid into and pulling cooling fluid out of the balloon 112 at a specified flow rate. In balloonless embodiments, the transducer 111 is not disposed within a balloon.

Figure 2C:
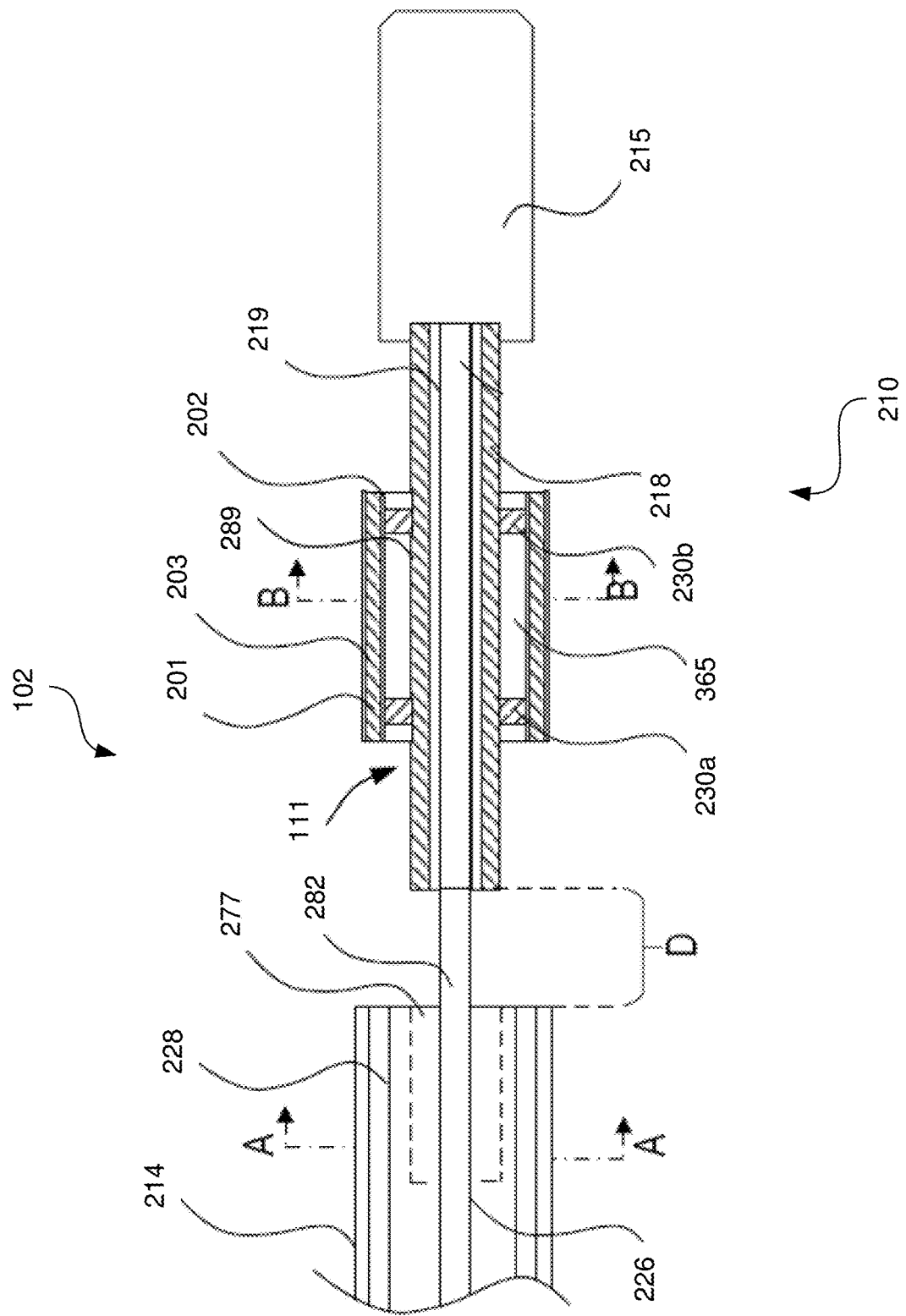
FIG. 2C illustrates a longitudinal cross-sectional view of a distal portion of a catheter of the ultrasound-based tissue treatment system in accordance with an embodiment of the present technology.
Figure 3B:
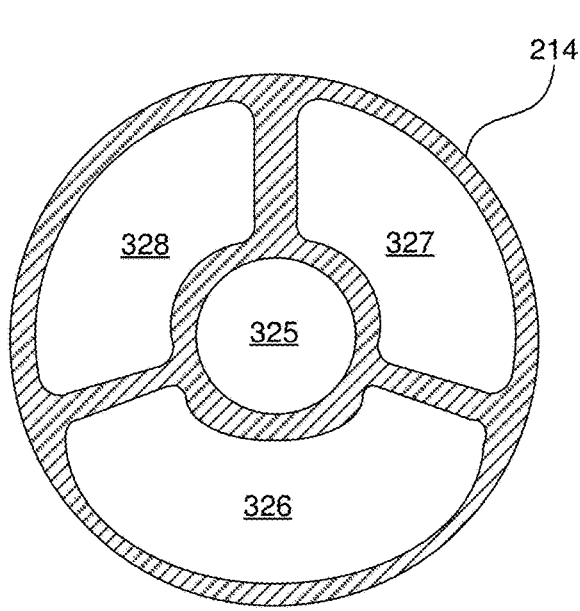
FIG. 3B illustrates a cross-sectional view across a portion of the ultrasound transducer of the catheter, along the line B-B in FIG. 2C.
Figure 3B:
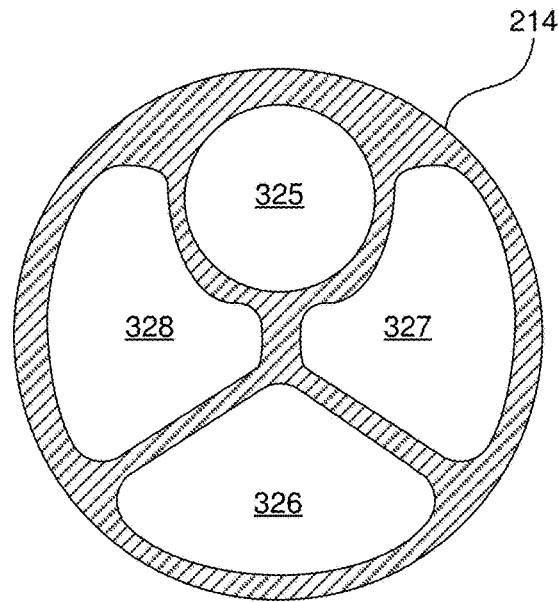
Figure 3B:
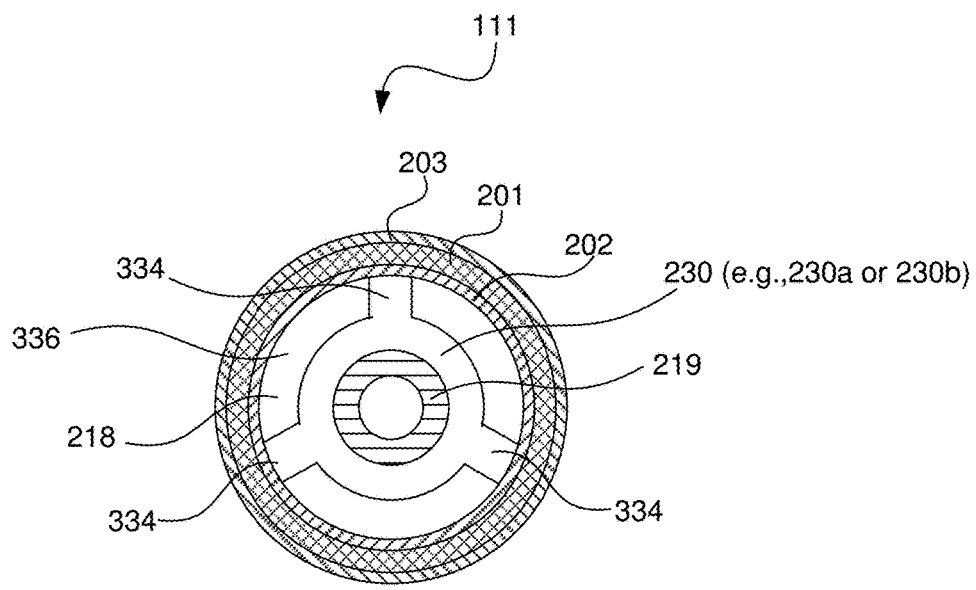

FIG. 2C illustrates a longitudinal cross-sectional view of the distal portion 210 of the catheter 102. FIG. 3A1 illustrates a cross-sectional view of the catheter shaft 214 along the line A-A shown in FIG. 2C, according to an embodiment. FIG. 3A2 illustrates a cross-sectional view of the catheter shaft 214 along the line A-A shown in FIG. 2C, according to an alternative embodiment. FIG. 3B illustrates a cross-sectional view of the ultrasound transducer 111 along the line B-B shown in FIG. 2C, according to an embodiment. In certain embodiments, the catheter shaft 214 may be about 1.8 mm in diameter. The catheter shaft 214 includes one or more lumens that may be used as fluid conduits, an electrical cabling passageway, a guidewire lumen and/or the like, as described in further detail below with reference to FIGS. 3A1 and 3A2. In certain embodiments suitable, e.g., for renal denervation, the guidewire 216 has a diameter of about 0.36 mm and a length of from about 180 cm to about 300 cm, and is delivered using a 7 French guide catheter, having a minimum inner diameter of 2.06 mm and a length less than about 80 cm. In certain embodiments, a 6 French guide catheter is used to deliver the guidewire 216. In certain embodiments, the guide catheter has a length of about 55 cm. In certain embodiments, the guide catheter has a length of about 85 cm and a hemostatic valve is attached to the hub of the guide catheter to allow for continuous irrigation of the guide catheter to decrease the risk of thromboembolism.

Referring again to FIG. 2C, the ultrasound transducer 111 may include a cylindrical hollow tube 201 made of a piezoelectric material (e.g., lead zirconate titanate (PZT), etc.), with inner and outer electrodes 202, 203 disposed on the inner and outer surfaces of the cylindrical tube 201, respectively. Such a cylindrical hollow tube of piezoelectric material is an example of, and thus can be referred to as, a piezoelectric transducer body 201. As will be described in additional detail below, a piezoelectric transducer body can have various other shapes and need not be hollow. In certain embodiments suitable, e.g., for renal denervation, the piezoelectric material, of which the piezoelectric transducer body 201 is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body (e.g., 201). Application of a voltage and alternating current across inner and outer electrodes 202, 203 causes the piezoelectric material to vibrate transverse to the longitudinal direction of the cylindrical tube 201 and radially emit ultrasonic waves. While the ultrasound transducer 111 in FIG. 2C is not shown as being surrounded by a balloon, it is noted that the ultrasound transducer 111 can be positioned within a balloon (e.g., 112), e.g., as shown in FIG. 2B.

As shown in FIG. 2C, the ultrasound transducer 111 is generally supported via a backing member or post 218. In certain embodiments, the backing member 218 comprises stainless steel coated with nickel and gold, wherein nickel is used as a bonding material between the stainless steel and gold plating. In certain embodiments suitable, e.g., for renal denervation, an outer diameter of the transducer 111 is about 1.5 mm, an inner diameter of the transducer 111 is about 1 mm, and the transducer 111 has a length of about 6 mm. Transducers having other inner diameter, outer diameters, and lengths, and more generally dimensions and shapes, are also within the scope of the embodiments described herein. Further, it is noted that the drawings in the FIGS. are not necessarily drawn to scale, an often are not drawn to scale.

As illustrated in FIG. 2C, the backing member 218 may extend from the distal portion 210 of the catheter shaft 214 to a distal tip 215. For example, the distal end of the backing member 218 may be positioned within an adjacent opening in the tip 215, and the proximal end of the backing member 218 may be moveably coupled to the distal portion 210 of the catheter shaft 214 via the electrical cabling 282. In other embodiments, there is a gap (e.g., labeled D in FIG. 2C) between the distal end of the catheter shaft 214 and the proximal end of the ultrasound transducer 111.

In order to permit liquid cooling along both the inner and outer electrodes 202, 203, the backing member 218 may include one or more stand-off assemblies 230a and 230b. The stand-off assemblies 230a, 230b may define one or more annular openings through which cooling fluid 213 may enter the space of the transducer 111 (which may be selectively insulated, in accordance with certain embodiments described below) between the backing member 218 and the inner electrode 202. Accordingly, the backing member 218 may serve as a fluid barrier between the cooling fluid 213 circulated within the balloon 112 and the lumen of the backing member 218 that receives the guidewire 216. As shown schematically in FIG. 2C, for example, the stand-off assemblies 230a, 230b of the backing member 218 may be positioned along or adjacent to each longitudinal end of the ultrasound transducer 111 (separated by a main post body 289) and couple the cylindrical tube 201 of the ultrasound transducer 111 to the backing member 218. With reference to FIG. 3B, a stand-off assembly 230 (230a or 230b) may have a plurality of lugs, ribs, or attachment points 334 that engage the inner electrode 202 of the transducer 111. In certain embodiments, the attachment points 334 are soldered to the inner electrode 202 of the transducer 111. The number, dimensions, and placement of the ribs 334 may vary, as desired or required. For example, as illustrated in FIG. 3B, a total of three ribs 334 can be generally equally-spaced apart from one another at an angle of 120 degrees apart from one another, defining openings 336 through which a cooling fluid or blood may enter an interior space of the cylindrical tube 201 between the inner electrode 202 disposed along the inner surface of the cylindrical tube 201 and the backing member 218. In certain embodiments, the maximum outer diameter of stand-off assemblies 230a and 230b is about 1 mm, the outer diameter of the main post body 289 is about 0.76 mm, and the inner diameter of backing member 218 is about 0.56 mm.

In accordance with certain embodiments, the stand-off assemblies 230a, 230b are electrically conductive, so as to electrically couple the inner electrode 202 of the ultrasound transducer 111 to the backing member 218. One or more conductors of the electrical cabling 282 may be electrically coupled to the backing member 218. Thus, as the controller 120 is activated, current may be delivered from the electrical cabling 282 to the inner electrode 202 of the ultrasound transducer 111 via the backing member 218 and the stand-off assemblies 230a, 230b, which advantageously eliminates the need to couple the cabling 282 directly to the inner electrode 202 of the transducer 111. In other embodiments, the backing member 218 and the stand-off assemblies 230a, 230b are made of one or more electrical insulator material (s), or if made of an electrically conductive material(s) are coated with one or more electrical insulator material(s).

Moreover, as illustrated in FIG. 2C, the backing member 218 may have an isolation tube 219 disposed along its interior surface so as to prevent or reduce the likelihood of electrical conduction between the guidewire 216 (shown in FIG. 2B) and the backing member 218, for use in embodiments where such an electrical conduction is not desired. The isolation tube 219 can be formed of a non-electrically conductive material (e.g., a polymer, such as polyimide), which can also be referred to as an electrical insulator. As illustrated in FIG. 2C, the isolation tube 219 may extend from the catheter shaft 214 through the lumen of the backing member 218 within the transducer 111 to the tip 215. In this manner, the transducer 111 is distally offset from the distal end of the catheter shaft 214.

As illustrated in FIG. 2C, the catheter 102 may also include a bore 277 extending from the distal end of the catheter 102 proximally within the catheter 102, and sized and shaped to receive at least a portion of the backing member 218, thereby electrically insulating the isolation tube 219 and/or the ultrasound transducer 111. Accordingly, during delivery of the catheter 102 to the anatomical region being treated, the backing member 218, the isolation tube 219, and/or the ultrasound transducer 111 may be at least partially retracted within the bore 277 of the catheter 102, e.g., by retracting the electrical cabling 282, thereby providing sufficient stiffness to the catheter 102 such that the catheter 102 may be delivered in a safe manner.

As illustrated in FIGS. 3A1 and 3A2, the catheter shaft 214 includes one or more lumens that can be used as fluid conduits, electrical cabling passageways, guidewire lumen, and/or the like. For example, as illustrated in FIGS. 3A1 and 3A2, the catheter shaft 214 may comprise a guidewire lumen 325 that is shaped, sized and otherwise configured to receive the guidewire 216. In certain embodiments, as illustrated in FIG. 3A1, the guidewire lumen 325 is located in the center of the catheter shaft 214 in order to center the transducer 111 within the catheter shaft 214. Alternatively, the guidewire lumen 325 can be offset from the center of the catheter shaft 214, e.g., as shown in FIG. 3A2. The catheter shaft 214 may also include a cable lumen 326 for receiving electrical cabling. Further, the catheter shaft 214 can include one or more fluid lumens 327, 328 for transferring the cooling fluid 213 (e.g., water, sterile water, saline, 5% dextrose (D5W)), other liquids or gases, etc., from and to a fluid source, e.g., the reservoir 110, at the proximal portion 220 of the catheter 102 (external to the patient) to the balloon 112 under control of the controller 120. Active cooling of about the first millimeter of tissue is designed to preserve the integrity of the blood vessel wall, e.g., the renal arterial wall.

The catheter 102 may include only a single fluid lumen or two or more fluid lumens (e.g., 3, 4, more than 4, etc.), as desired or required. As illustrated in FIG. 3A1, in an embodiment, the fluid lumens 327 and 328 and the cable lumen 326 all having a kidney-shaped or D-shaped cross-sections configured to maximizes efficiency of fluid flow delivery and distribute fluid uniformly across the ultrasound transducer 111 by maximizing area, while minimizing the perimeter of the fluid lumens 327 and 328. In certain embodiments, each of the fluid lumens 327 and 328 and the cable lumen 326 are substantially symmetrical, the same size, the same geometry, and/or are interchangeable, e.g., as shown in FIG. 3A1. Changes in fluid flow rate within the catheter can lead to delayed or incomplete treatment. In certain embodiments, the catheter shaft 214 is configured to enable a fluid flow rate of about 40 mL/min. In certain embodiments, the catheter shaft 214 is configured to enable a fluid flow rate of about 35 to 45 mL/min. In certain embodiments, the catheter shaft 214 is configured to enable a fluid flow rate of about 20 to 45 mL/min. In certain embodiments, e.g., suitable for radial delivery during a renal denervation procedure, the catheter shaft 214 is configured to enable a fluid flow rate of about 10 to 20 mL/min. Each of one or more lumens (e.g., 328) may be in fluid communication with the same or separate, individual fluid sources external to the patient at the proximal portion 220 of the catheter 102.

As another example, the catheter shaft 214 may include any suitable number of fluid lumens for transferring the cooling fluid to and from the balloon 112 (or to the transducer 111 in balloonless embodiments) from the reservoir 110 responsive to instructions executed by the controller 120. In certain balloonless embodiments, the catheter shaft 214 may omit fluid lumens 327, 328 and the system 100 may omit the reservoir 110. In certain balloonless embodiments, the catheter shaft 214 includes the fluid lumens 327, 328 and the system 100 includes the reservoir 110.

In certain embodiments, as illustrated in FIG. 3A2, the guidewire lumen 225 is located proximal to and/or shares a wall with the catheter shaft 214 so as to enable expedited exchange of catheters during a procedure. In such embodiments, the cable lumen 326 may be located opposite the guidewire lumen 225 and also share a wall with the catheter shaft 214. The cable lumen 326 may be, e.g., triangular or rectangular in shape, and may be configured to maximize the area available for and minimize the perimeter of the fluid lumens 327 and 328, thereby enabling a higher flow rate for the same pressure. The fluid lumens 327 and 328 may be shaped so as to optimize flow rate and decrease drag of the catheter 102. In such embodiments, the area of fluid lumens 327 and 328 may not be maximized, but instead the walls of the fluid lumens 327 and 328 may be rounded to avoid pockets that may otherwise cause drag, thereby optimizing flow rate of the cooling fluid 213 within the fluid lumens 327 and 328.

The catheter shaft 214 may include within at least the cable lumen 326, the electrical cabling 282 (e.g., a coaxial cable, parallel coaxial cables, a shielded parallel pair cable, one or more wires, or one or more other electrical conductors) coupling the inner and outer electrodes 202, 203 of the ultrasound transducer 111 to the controller 120, such that the controller 120 may apply a suitable voltage across such electrodes so as to cause the piezoelectric material of the transducer 111 to emit ultrasonic energy to a subject. In certain embodiments, the cable lumen 326 is shaped, sized and otherwise configured to receive the electrical cabling 282 (e.g., coaxial cable(s), wire(s), other electrical conductor(s), etc.). The electrical cabling 282 permits the electrodes 202, 203 of the ultrasound transducer 111 to be selectively activated in order to emit acoustic energy to a subject. More specifically, the electrical cabling 282 can allow for the communication of transducer information, such as operating frequency and power, from the catheter 102 to the controller 120 and/or vice versa, as well as the transfer of electrical energy to the ultrasound transducer 111 during a procedure.

The distal portion 210 of the catheter 102 may be percutaneously delivered to the target anatomical location (e.g., at a specified location within the body lumen BL) via any suitable intraluminal access route, e.g., via a gastrointestinal route or via an intravascular route such as the femoral or radial route. In certain embodiments, the controller 120 is configured so as to fill the balloon 112 with the cooling fluid 213 only after the distal portion 210 of the catheter 102 is suitably positioned at the target anatomical location. The catheter 102 may be delivered through the body lumen BL with or without the assistance of a commercially-available guidewire. For example, the catheter 102 and the balloon 112 may be delivered over the guidewire 216 (shown in FIG. 2B) and through a renal guide catheter. For further examples of guidewire-based delivery of ultrasound transducers, see U.S. Pat. No. 10,456,605, which was incorporated herein by reference above. However, it should be appreciated that any suitable steerable catheter or sheath, or any other suitable guiding device or method, may be used to deliver the distal portion 210 of the catheter 102 to a target anatomical location of the subject. Once delivered to a suitable location within the body lumen BL, the balloon 112 may be inflated with the cooling fluid 213 (e.g., under control of controller 120), and the transducer 111 may be actuated (e.g., by applying a voltage across the inner and outer electrodes 202, 203 under control of the controller 120) so as to deliver unfocused ultrasonic energy to the target anatomical location. The transducer 111 is sized for insertion in the body lumen BL and, in the case of insertion of the renal artery, for example, the transducer 111 may have an outer diameter of less than 2 mm, for example, about 1.5 mm and an inner diameter of less than 1.8 mm, for example, about 1 mm. As described in greater detail below, the length L of the transducer 111 optionally may be selected such that the ultrasonic waves that it generates has a near field depth suitable for generating a lesion only within a desired region relative to the wall of a target body lumen BL.

Referring to FIGS. 1, 2A, 2C, 3A1, and 3A2, in accordance with certain embodiments, a proximal end of the connection cable 140 connects to the controller 120, and the distal end of the connection cable 140 connects to the electrical coupling(s) 232 on the proximal portion of the catheter 102. The electrical cabling 282 extends through a cable lumen (e.g., 326 in FIG. 3A1 or 3A2) of the catheter shaft 214 to the electrical coupling(s) 232, to thereby electrically couple the transducer 111 to the electrical coupling(s) 232. By having the connection cable 140 electrically coupled between the controller 120 and the electrical coupling(s) 232, and the electrical cabling 282 electrically coupled between the electrical coupling(s) 232 and the transducer 111, the controller 120 is electrically coupled to the transducer 111 to thereby provide power to, and otherwise control, the transducer 111.

It will be appreciated that the frequency, power, and amount of time for which the transducer 111 is actuated suitably may be selected based on the treatment to be performed. For example, the frequency optionally is in a range of from 1 to 20 MHz, e.g., 1-5 MHz, 5-10 MHz, 8.5-9.5 MHz, 10-15 MHz, 15-20 MHz, or 8-10 MHz, for example, about 9 MHz. Or, for example, the frequency optionally is in a range of below 1 MHz, e.g., 0.1-0.2 MHz, 0.2-0.3 MHz, 0.3-0.4 MHz, 0.4-0.5 MHz, 0.5-0.6 MHz, 0.6-0.7 MHz, 0.7-0.8 MHz, 0.8-0.9 MHz, or 0.9-1.0 MHz. Or, for example, the frequency optionally is in a range of above 20 MHz, e.g., 20-25 MHz, 25-30 MHz, or above 30 MHz. Optionally, the power may be in a range of 5 to 80 W (e.g., 5 to 50 W, 5 to 10 W, 12.1-16.6 W, 10 to 20 W, 20 to 30 W, 30 to 40 W, 40 to 50 W, 50 to 60 W, 60 to 70 W, or 70 to 80 W, or may be more than 80 W). For example, the power may be 20 to 40 W with 20 to 30 W for balloons with smaller diameters (e.g., 3.5 to 5 mm) and 30 to 40 W for balloons with larger diameters (e.g., 5 to 8 mm). The period of time during which the transducer 111 is actuated may be sufficient to complete the particular treatment being performed, and may depend on factors such as the power at the transducer, the frequency of ultrasonic energy emitted, the size of the tissue region being treated, the age, weight and gender of the patient being treated, and/or the like. Illustratively, in some configurations the time period for which the transducer 111 may be actuated may be in a range of about 3 seconds to 5 minutes, e.g., 3-10 seconds, 3-30 seconds, 30 seconds to 1 minute, 30 seconds to 5 minutes, 1 to 3 minutes, about 2 minutes, 10 seconds to 1 minute, 1 to 2 minutes, 2 to 3 minutes, 3 to 4 minutes, or 4 to 5 minutes. Or, for example, the transducer 111 may be actuated for less than 10 seconds (s), e.g., 0.1-10 s, 1-2 s, 2-3 s, 3-4 s, 4-5 s, 5-6 s, 6-7 s, 7-8 s, 8-9 s, or 9-10 s. Or, for example, the transducer 111 may be actuated for more than 5 minutes (m), e.g., 5-6 m, 6-7 m, 7-8 m, 8-9 m, 9-10 m, 10-15 m, 15-20 m, or for more than 20 minutes.

In various configurations, the delivery of ultrasound energy during the treatment may be continuous or substantially continuous, e.g., without any interruptions or fluctuations in frequency, power, duty cycle and/or any other parameters. Alternatively, one or more of the frequency, power, duty cycle, or any other parameter may be modified during the treatment. For example, in some configurations, the delivery of ultrasonic energy is modulated, e.g., between on and off, or between a relatively high level and a relatively low level, so as prevent or reduce the likelihood of overheating of adjacent (e.g., targeted or non-targeted) tissue. For examples of such modulation, see U.S. Pat. No. 10,499,937 to Warnking, the entire contents of which are incorporated herein by reference.

In example configurations in which nerve tissue is to be treated, e.g., the nerves N illustrated in FIG. 2B, the transducer 111 (or 411, 511, 811, 911, 1011, or 111, etc.) may be positioned and configured so as to deliver ultrasonic energy through the wall of a body lumen BL that is adjacent to that nerve tissue, e.g., through the wall of the body lumen BL. In one nonlimiting example, renal nerves to be treated using the transducer 111 may be located about 0.5 mm to 8 mm (e.g., about 1 mm to 6 mm) from the inner wall of the renal artery. In other examples, nerve tissue to be treated may be located less about 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, less than 0.5 mm, or more than 8 mm from the inner wall of a body lumen in which transducer is disposed. Under control of the controller 120, the transducer 111 (or 411, 511, 811, 911, 1011, or 111, etc.) generates unfocused ultrasonic energy that heats any suitable nerve tissue so as to at least partially neuromodulate such nerve tissue, e.g., cause complete or partial ablation, necrosis, or stimulation of such nerve tissue. The ultrasonic energy generated by the transducer 111 (or 411, 511, 811, 911, 1011, or 111, etc.) may radiate radially outward so as to target the nerve tissue regardless of the radial orientation of such nerve tissue relative to the body lumen. In some configurations, the unfocused ultrasonic energy is delivered along an entire, continuous circumference of the transducer 111 (or 411, 511, 811, 911, 1011, or 111, etc.). In other configurations, the ultrasonic energy is emitted non-continuously or intermittently around the circumference of the transducer 111 (or 411, 511, 811, 911, 1011, or 111, etc.). It should be appreciated that nerve tissue, and more specifically the renal nerves, are only one example of tissue that may be treated using an ultrasound transducer. Other examples of target anatomical regions that may be treated with an ultrasound transducer 111 are described elsewhere herein.

Regardless of the particular shape or extent of the acoustic energy that the transducer delivers to the target anatomical region, the cooling fluid 213 within the balloon 112 surrounding the transducer may protect certain tissue of the subject. For example, the cooling fluid 213 may prevent or reduce the likelihood of stenosis or other damage to the wall of the body lumen BL through which energy is delivered during the treatment. In some configurations, cooling fluid 213 flows across one or both of the exterior and interior surfaces of the transducer 111 (or 411, 511, 811, 911, 1011, or 111, etc.), e.g., may directly contact one or both of the exterior and interior surfaces of the transducer. In certain embodiments, described in more detail below, an electrical insulator of a transducer inhibits electrical shorting between electrodes of the transducer via an electrically conductive cooling liquid 213, or via blood. The terms "short," "short circuit," "electrical short," and the like, as used herein, are used interchangeably and refer to any conductive path with an impedance of less than 10,000 ohms. Accordingly, where there is a "short" between a pair of electrodes, that means there is conductive path with an impedance of less than 10,000 ohms between the pair of electrodes, wherein such a conductive path can be provided by an electrically conductive fluid, but is not limited thereto.

Selectively Insulated Transducers

Referring briefly back to FIG. 2B, in accordance with certain embodiments the ultrasound transducer 111 is disposed partially or completely within the balloon 112. As explained above, in the initial discussion of FIG. 2B, the balloon 112 may be inflated with a cooling fluid 213 so as to contact the interior surface (e.g., intima) of the body lumen BL. More specifically, the cooling fluid 213 is circulated around the ultrasound transducer 111 to actively cool the region of treatment. Use of a cooling fluid 213 that is electrically non-conductive preserves electrical isolation between the inner and outer electrodes 202 and 203 of the ultrasound transducer 111. However, medical personnel must stock and remember to use an electrically non-conductive cooling fluid 213. For the convenience of the medical personnel, the ultrasound transducers according to certain embodiments described herein are designed to properly operate when surrounded by or otherwise exposed to an electrically conductive fluid, such as, but not limited to, saline. As will be appreciated from the discussion below, such embodiments are implemented by insulating at least a portion of the ultrasound transducer 111. Where the ultrasound transducer is partially insulated, such that it can operate properly when used with an electrically conductive cooling fluid or is otherwise exposed to an electrically conductive fluid, such as blood, the transducer may be generally referred to as a selectively insulated transducer or partially insulated transducer, or more succinctly, as a transducer.

Beneficially, the selectively insulated transducers disclosed herein allow for use of a cooling fluid (e.g., 213) which is electrically conductive and/or use of a patient's own blood flow to cool the transducers. More specifically, the selectively insulated transducers disclosed herein may be configured so as to include at least one electrical insulator which inhibits (and preferably prevents) shorting between electrodes (e.g., 202 and 203) of the transducers via an electrically conductive fluid that is either within a balloon or is blood. Illustratively, the present insulated transducers may include a hollow cylindrical tube (e.g., 201) made of a piezoelectric material, which may be disposed within a balloon, and includes an inner surface and an outer surface. In certain embodiments, such as those described above, the transducer is cylindrical. An inner electrode (e.g., 202) may be disposed on the inner surface of the hollow cylindrical tube (e.g., 201), and an outer electrode (e.g., 203) may be disposed on the outer surface of the hollow cylindrical tube (e.g., 201) of the transducer. The outer electrode, or the inner electrode, may have an electrical insulator covering the electrode to inhibit an electrical short between the outer electrode (e.g., 203) and the inner electrode (e.g., 202) via an electrically conductive fluid.

The piezoelectric material that makes up the hollow cylindrical tube (e.g., 201) may be actuated by applying a voltage across the inner electrode (e.g., 202) and the outer electrode (e.g., 203) in a manner such as known in the art, e.g., by a suitably programmed controller (e.g., 120) in electrical communication with the inner electrode and the outer electrode. In the absence of the present electrical insulator(s), in the absence of a balloon, or if a balloon is filled with an electrically conductive fluid, then applying a voltage across the inner and outer electrodes (e.g., 202 and 203) may cause an electrical short that inhibits the piezoelectric material from generating an ultrasonic wave. In the absence of the present electrical insulator(s), such shorting may be inhibited by instead using a non-conductive fluid within a balloon, such as suitably deionized water or dextrose, that itself may provide insulation between the inner and outer electrodes. However, it may be less convenient to use such a non-electrically conductive fluid within a surgical setting. For example, hospitals and other treatment centers typically do not maintain a source of deionized water within its surgery wards. The selectively insulated transducers described herein allow for electrically conductive fluids, which are readily available throughout hospitals and other treatments centers, to be used within balloons, and thus may enhance ease of integrating the present systems into surgical settings. Examples of electrically conductive fluids, which are readily available throughout hospitals and other treatments centers, include saline, non-pure water, or sodium lactate solution. Sodium lactate solution, which is also known as Ringer's lactate solution, lactated Ringer's solution, or Hartmann's solution, is a type of isotonic, crystalloid fluid further classified as a balanced or buffered solution used for fluid replacement. Such a sodium lactate solution includes sodium, chloride, potassium, calcium, and lactate in the form of sodium lactate, mixed into a solution with an osmolarity of 273 mOsm/L and pH of about 6.5.

In certain embodiments, a balloonless catheter may be used, in which case blood, which is electrically conductive, flowing within a body lumen would be used to cool the transducer. The requirement of using a balloon adds time and complexity to the procedure, as the physician may need to use multiple balloons and catheters during a single procedure. In addition, failure to use the correct balloon size may result in renal artery dissection, perforation, aneurysm, significant vasospasm requiring intervention, ablation of unintended tissues or structures, or no ablation of target tissue achieved. Further, some arteries, e.g., accessory arteries, may not be treatable due to balloon size constraints. Untreated accessory arteries may be predictive of decreased response to renal denervation. The inflated balloon should be opposed to the wall of the renal artery to maximize tissue ablation, and multiple inflations of the balloon to achieve apposition of the balloon to the renal artery wall may result in increased vessel trauma. Beneficially, the selectively insulated transducers disclosed herein allow for use of a balloonless catheter, wherein the patient's own blood flow is used as a cooling fluid.

Figure 4A:
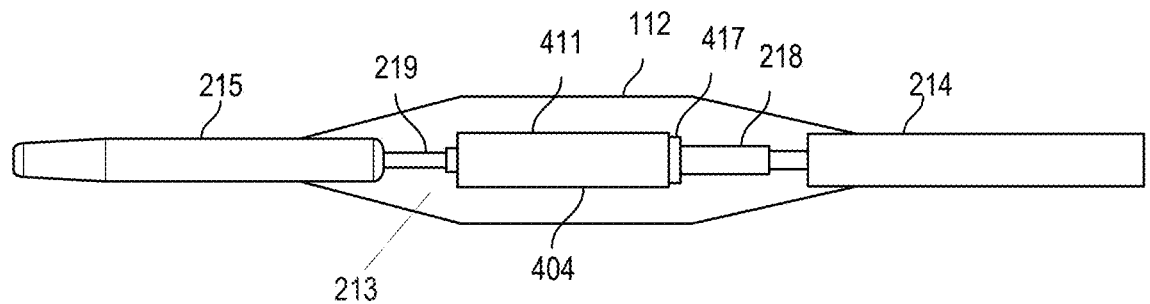
FIG. 4A is a side view of a distal portion of a catheter of an ultrasound-based tissue treatment system including a selectively insulated transducer in accordance with certain embodiments of the present technology.
Figure 4B:
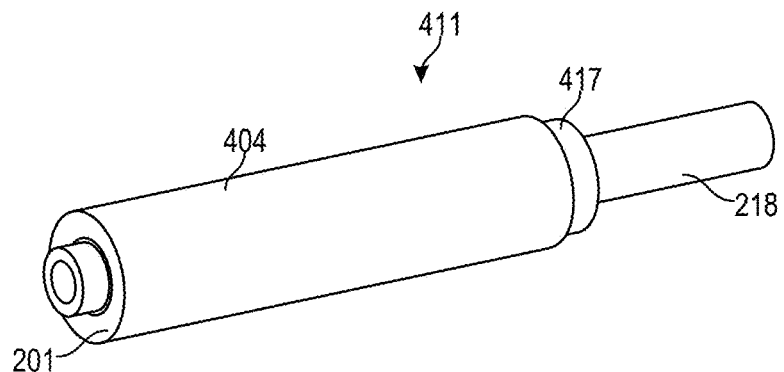
FIG. 4B is a perspective view of the selectively insulated transducer in accordance with certain embodiments of the present technology, wherein an outer electrode of a piezoelectric transducer is covered by an electrical insulator.
Figure 4C:
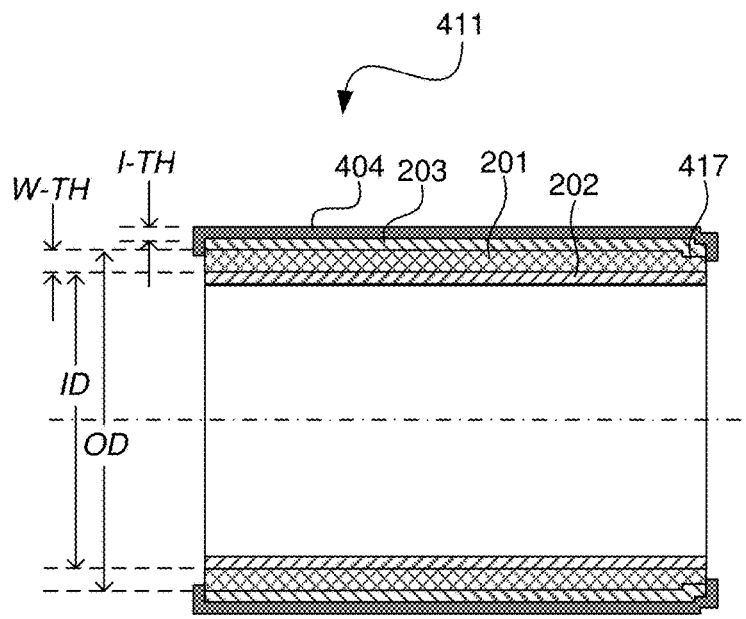
FIG. 4C illustrates a longitudinal cross-sectional view of the selectively insulated transducer introduced in FIGS. 4A and 4B.
Figure 4D:
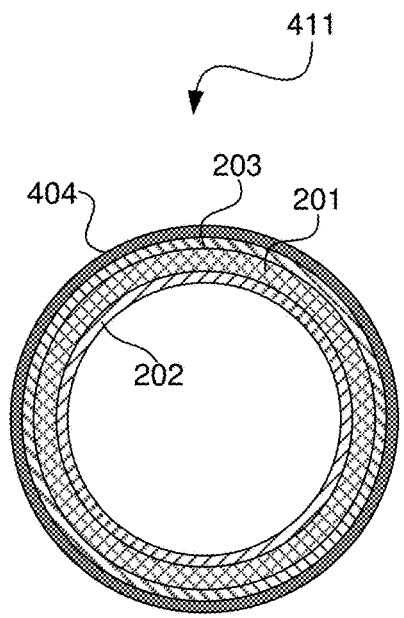
FIG. 4D illustrates a radial cross-sectional view of the selectively insulated transducer introduced in FIGS. 4A and 4B.

FIG. 4A is a side view of a distal portion of a catheter (e.g., 102) of an ultrasound-based tissue treatment system (e.g., 100) including a selectively insulated transducer 411 in accordance with certain embodiments of the present technology. The selectively insulated transducer 411 can also be referred to more succinctly as a selectively insulated transducer 411, or even more succinctly as a transducer 411. FIG. 4B is a perspective view of the selectively insulated transducer 411 in accordance with certain embodiments of the present technology, wherein an outer electrode (e.g., 203) of a piezoelectric transducer body (e.g., 202) is covered by an electrical insulator 404. FIGS. 4C and 4D illustrate, respectively, a longitudinal cross-sectional view and a radial cross-sectional view of the selectively insulated transducer 411 introduced in FIGS. 4A and 4B.

In the embodiments of FIGS. 4A-4D, the piezoelectric transducer body 201 comprises a hollow tube of piezoelectric material having an inner surface and an outer surface, with the inner electrode 202 disposed on the inner surface of the hollow tube of piezoelectric material, and the outer electrode 203 disposed on the outer surface of the hollow tube of piezoelectric material. In such embodiments, the hollow tube of piezoelectric material is an example of the piezoelectric transducer body 201. In FIGS. 4A-4D, the hollow tube of piezoelectric material, or more generally the piezoelectric transducer body 201, is cylindrically shaped and has a circular radial cross-section, as can be appreciated from FIG. 4D. However, in alternative embodiments the hollow tube of piezoelectric material can have other shapes besides being cylindrical with a circular radial cross-section. Other cross-sectional shapes for the hollow tube of piezoelectric material, and more generally the piezoelectric transducer body 201, include, but are not limited to, an oval or elliptical cross-section, a square or rectangular cross-section, pentagonal cross-section, a hexagonal cross-section, a heptagonal cross-section, an octagonal cross-section, and/or the like.

The hollow tube of piezoelectric material, and more generally the piezoelectric transducer body 201, can be made from various different types of piezoelectric material, such as, but not limited to, lead zirconate titanate (PZT), polyvinylidene fluoride (PVDF), or other presently available or future developed piezoelectric ceramic materials. As depicted in FIGS. 4A-4C, the transducer 411 may include a stepped portion 417, as described in U.S. Pat. No. 10,456,605, the entire contents of which are incorporated herein by reference. In certain embodiments, the stepped portion 417 on the proximal end of the transducer 411 allows for attachment of the electrical cabling 282, e.g., via parallel wires (not shown), that delivers energy to the transducer 411. In certain embodiments, electrical cabling 282 comprises parallel coaxial cables having a combined impedance of about 50 ohms. Such a stepped portion 417 can be incorporated into any of the transducers described herein. It would also be possible for both the proximal and distal ends of a transducer to include a stepped portion (the same as or similar to 417), which embodiments can be referred to as dual stepped embodiments.

Referring to FIG. 4C, in accordance with certain embodiments, which are suitable for a renal denervation procedure, an outer diameter (OD) of the piezoelectric transducer body 201 is within the range of about 1.3 mm to 1.7 mm, and an inner diameter (ID) of the piezoelectric transducer body 201 is within the range of about 0.8 mm to 1.2 mm. In specific embodiments, the OD is about 1.5 mm and the ID is about 1 mm. In accordance with certain embodiments, a wall thickness (W-TH) of the piezoelectric material of the piezoelectric transducer body 201, between its inner diameter (ID) and its outer diameter (OD), is within the range of 0.2 mm and 1.0 mm. More specifically, the wall thickness (W-TH) can be in the range of 0.2 mm and 0.5 mm. Even more specifically, the wall thickness (W-TH) can be in the range of 0.24 mm and 0.26 mm (and even more specifically, can be 0.25 mm+/−0.01 mm), which can provide for an ultrasound transducer that produces acoustical energy have a frequency of approximately 9 MHz. In certain embodiments, the ultrasound transducers (e.g., 211, 411, 511, 811, 911, 1011, 1211, etc.) described herein are configured to deliver acoustic energy in the frequency range of 8.5 to 9.5 MHz. In certain embodiments, such transducers are configured to deliver acoustic energy in the frequency range of 8.7-9.3 MHz or 8.695-9.304 MHz. Transducers delivering acoustic energy in the frequency range of 8.7-9.3 MHz have been shown to produce ablation up to mean depths of 6 mm. The piezoelectric transducer body 201 and the outer and inner electrodes 203, 202 may be formed using any suitable method, such as the methods described in U.S. Pat. No. 10,140,041 to Taylor, the entire contents of which are incorporated herein by reference. The thickness (I-TH) of the electrical insulator 404 (and the other electrical insulators described herein) can be in the range of about 10 µm to 20 µm thick, but are not limited thereto. The above described dimensions and thicknesses, while described with reference to the embodiments shown in FIGS. 4A-4D, also apply to the other embodiments described herein, including the embodiments described below.

In the embodiments of FIGS. 4A-4D, an electrical insulator is not disposed on the inner electrode 202. In other words, in the embodiments of FIGS. 4A-4D, with respect to the inner and outer electrodes 202, 203, only the outer electrode 203 is covered by the electrical insulator 404. In such embodiments, the electrical insulator 404 that is disposed on and covers the outer electrode 203 inhibits (and preferably prevents) the outer electrode 203 from coming into contact with an electrically conductive fluid (e.g., 213) when the ultrasound transducer 411 is positioned in the electrically conductive fluid. In other words, in such embodiments the electrical insulator 404 provides for both electrical isolation and physical isolation from an electrically conductive fluid that the transducer is placed within. However, since an electrical insulator is not disposed on the inner electrode 202, the inner electrode 202 may come into contact with an electrically conductive fluid when the ultrasound transducer 411 is positioned in the electrically conductive fluid (e.g., 213). In such embodiments, the electrical insulator 404 that is disposed on the outer electrode 203 inhibits (and preferably prevents) electrical conduction between the inner electrode 202 and the outer electrode 203 when the ultrasound transducer 411 is placed within an electrically conductive fluid. The piezoelectric transducer body 201 is configured to generate ultrasonic waves in response to a voltage being applied between the inner and outer electrodes 202, 203. The electrical insulator 404 inhibits (and preferably prevents) a short circuit from occurring between the inner and outer electrodes 202, 203 when the ultrasound transducer 411 is placed within the electrically conductive fluid and a voltage is applied between the inner and outer electrodes 202, 203. More specifically, the controller 120 may be electrically coupled to inner and outer electrodes 202, 203 vial electrical cabling 282, and may actuate the selectively insulated transducer 411 (or any of the other selectively insulated transducers described herein) by applying a voltage between the inner and outer electrodes 202, 203 (or any other pair of electrodes described herein), so as to cause the piezoelectric material of the piezoelectric transducer body 201 to generate an unfocused ultrasonic wave that radiates radially outwardly.

In certain embodiments, the ultrasound transducer 411 is placed within a balloon (e.g., 112) that is at least partially filled with cooling fluid (e.g., 213), that is an electrically conductive fluid, which is used to cool a portion of a body lumen BL within which the ultrasound transducer 411 may be positioned. The electrically conductive fluid, that the balloon is at least partially filled with, can for example be saline, non-pure water, or sodium lactate solution, or a combination thereof, but is not limited thereto. In alternative embodiments, which can be referred to as balloonless embodiments, the ultrasound transducer 411 is directly exposed to blood flowing through a body lumen BL within which the ultrasound transducer may be positioned, in which case the electrically conductive fluid comprises the blood. In certain embodiments the electrical insulator 404 is parylene, and more specifically, a parylene conformal coating.

Materials from which the electrical insulator 404 can be made include, but are not limited to, parylene, cyanoacetate, epoxy resin, nylon, polytetrafluoroethylene (PTFE), polyimide, polyethylene, polyethylene terephthalate, polyvinyl chloride (PVC), or combinations thereof. In certain embodiments, parylene C is used to coat an electrode comprising gold using a chemical vapor deposition method as described, for example, in U.S. Pat. No. 5,908,506. For another example, the electrical insulator 404 can be a synthetic diamond coating, which can, for example, to deposited using chemical vapor deposition (CVD). In an embodiment, the surface of the electrode is treated with an adhesion promotion agent, e.g., silane, titanium (Ti), silicon oxide (SiOx), diamond-like carbon (DLC), tetramethylsilane (TMS) and aluminium oxide (AlOx), a solution of 1 gram 2-methylthio ethyl methacrylate, or 1 gram of 4-chlorothiophenol diluted in 1 L propanol (available from Th. Geyer GmbH & Co. KG, headquarter in Renningen, Germany), or AdPro Plus® or AdPro Poly® available from Specialty Coating Systems, Inc. (headquartered in Indianapolis, Indiana, USA), as well as other numerous other suppliers, prior to being coated with the electrical insulator 404, e.g., parylene. In certain embodiments, plasma surface-treatment methods may be used to prevent parylene delamination. It is noted that polytetrafluoroethylene (PTFE) is often marketed using the trademark TEFLON™, which is a registered trademark of The Chemours Company (headquartered in Wilmington, Delaware, USA), and that polyimide is often marketed using the trademark KAPTON™, which is a registered trademark of DuPont, also headquartered in Wilmington, Delaware, USA). In a specific embodiment, the peripheral surface of the outer electrode 203 is covered by a parylene coating, and the opposing longitudinal ends of the outer electrode 203 are covered by an epoxy resin. Other combinations of the aforementioned electrical insulator materials are also possible and within the scope of the embodiments described herein.

Various different types of parylene coatings can be used, wherein such parylene coatings can be conformal coatings that are ultra-thin, pinhole-free polymer coatings that have excellent moisture, chemical and dielectric barrier properties, thermal and ultraviolet (UV) stability, and dry-film lubricity. Example types of parylene include parylene N, parylene C, and paralyne D, but are not limited thereto.

As noted above, the thickness of the electrical insulator (e.g., 404, and the other electrical insulators described herein) can be in the range of about 10 μm to 20 μm thick, but are not limited thereto. In accordance with certain embodiments, and adhesion promoter can be included between an electrode (e.g., the outer electrode 203) and the electrical insulator (e.g., 404) to improve the adhesion of the electrical insulator to the electrode. To reduce the chance of there being small pinholes in the electrical insulator (e.g., 404) that would result in undesirable electrical leakage, multiple layers or coatings of the electrical insulator material may be applied, during multiple coating cycles. For an example, where the electrical insulator is to be a parylene coating having a 15 μm thickness, the coating can be deposited on the electrode in three separate coating cycles, each of which provides a coating thickness of 5 μm, to collectively provide the parylene coating having the 15 μm thickness.

The inner electrode 202 and outer electrode 203 may be made of the same electrically conductive material(s) as one another, or of different electrically conductive material(s) than one another. Examples of electrically conductive materials suitable for use as the inner and outer electrodes 202, 203 include copper, silver, and gold, and/or combinations thereof. In certain embodiments, nickel may be used as a barrier layer to prevent lead from degrading gold-plated electrodes. Example thicknesses of inner electrodes 202 and outer electrode 203 include about 120 microinches. In certain embodiments, the electrodes 202, 203 comprise a base coat of about 15 microinches of electroless copper, a second coat of about 102 to 120 microinches of high phosphorous electroless nickel, and a third coat of about 5 microinches of electroplated gold. The metal layers provide a way to solder electrical cabling 282, e.g., parallel coaxial cables, to the surfaces of the tube without damaging the piezoelectric material as well as allowing an even application of an electrical load to the transducer. In certain embodiments, the metal layers of the electrode coating are configured to produce an electrode that does not flake or peel due to mechanical or thermal loading and that supplies an even electrical load during sonication. The inner and outer electrodes 202, 203 may have the same thickness as one another, or they may have different thicknesses than one another. The inner and outer electrodes 202, 203 may be formed using any suitable method(s), such as, but not limited to, electroless plating and vapor deposition.

In order to apply a voltage between the inner and outer electrodes 202, 203 (or any other electrodes) of a transducer disclosed herein, or more generally provide input power to the transducer, cabling (e.g., 282) is connected between the controller 120 (or some other voltage source) and the electrodes of the transducer to provide electrical connections between the controller 120 (or some other voltage source) and the electrodes. For example, one or more coaxial cables or other types of electrically conductive wiring can be soldered to the electrodes of a transducer. One of the electrodes of a transducer can be coated and thereby covered with an electrical insulator before or after such cabling is attached to the electrodes. If the electrical insulator is applied to the electrode before the cabling (e.g., 282) is attached (e.g., soldered) to the electrodes, then a portion of the electrical insulator should be removed (e.g., using etching) or left uninsulated (e.g., using a mask) so that the cabling (e.g., 282) can be soldered or otherwise attached to the electrode(s). After the soldering or other type of attachment, the solder ball, or the like, should be covered with an electrically insulator, such as an epoxy resin, but not limited thereto. In other words, the point of contact between the cabling (which includes one or more cables) and the electrode (that is to be insulated) should also be insulated. Otherwise, exposing the solder ball (or other electrical contact point between a cable and the electrode) to an electrically conductive fluid would be the equivalent of exposing the entire electrode to the electrically conductive fluid. More generally, where cabling is to be connected to one of the electrodes that is covered with an electrical insulator, care should be used to ensure that no electrically conductive portion of the cabling or the attachment mechanism (e.g., a solder ball) will be exposed to an electrically conductive fluid when the transducer is in use. This is applicable to the transducer 411, as well as the other selectively insulated transducers described herein (e.g., 511, 911, 1011, etc.)

Figure 5A:
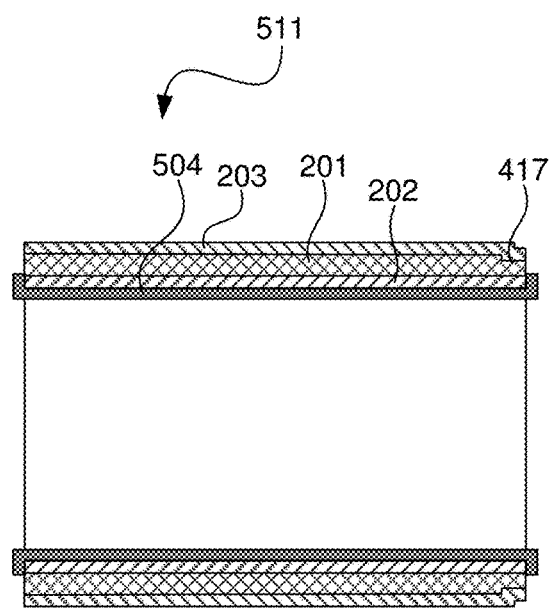
FIG. 5A illustrates a longitudinal cross-sectional view of the selectively insulated transducer according to another embodiment of the present technology, wherein an inner electrode of the piezoelectric transducer is covered by an electrical insulator.
Figure 5B:
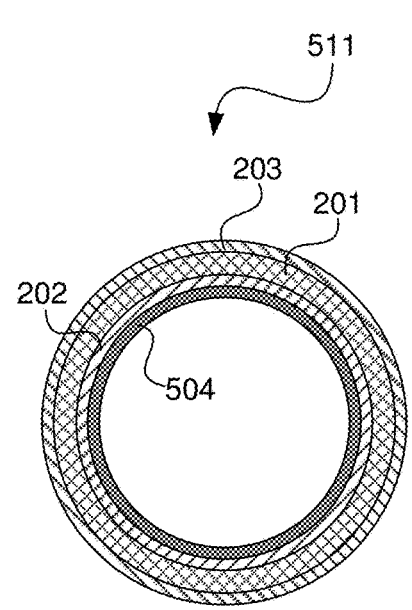
FIG. 5B illustrates a radial cross-sectional view of the selectively insulated transducer introduced in FIG. 5A, wherein the inner electrode of the piezoelectric transducer is covered by the electrical insulator.

FIGS. 5A and 5B illustrate, respectively a longitudinal cross-sectional view and a radial-cross sectional view, of a selectively insulated transducer 511 according to another embodiment of the present technology, wherein the inner electrode 202 of the piezoelectric transducer body 201 is covered by an electrical insulator 504. In such embodiments, the electrical insulator 504 that is disposed on and covers the inner electrode 202 inhibits (and preferably prevents) the inner electrode 202 from coming into contact with an electrically conductive fluid (e.g., 213) when the ultrasound transducer 511 is positioned in the electrically conductive fluid. In other words, in such embodiments the electrical insulator 504 provides for both electrical isolation and physical isolation from an electrically conductive fluid that the transducer is placed within. However, since an electrical insulator is not disposed on the outer electrode 203, the outer electrode 203 may come into contact with an electrically conductive fluid when the ultrasound transducer 511 is positioned in an electrically conductive fluid (e.g., 213). In such embodiments, the electrical insulator 504 that is disposed on the inner electrode 202 inhibits (and preferably prevents) electrical conduction between the inner electrode 202 and the outer electrode 203 when the ultrasound transducer 511 is placed within an electrically conductive fluid. The electrical insulator 504 inhibits (and preferably prevents) a short circuit from occurring between the inner and outer electrodes 202, 203 when the ultrasound transducer 511 is placed within an electrically conductive fluid and a voltage is applied between the inner and outer electrodes 202, 203.

In certain embodiments, the ultrasound transducer 511 is placed within a balloon (e.g., 112) that is at least partially filled with cooling fluid (e.g., 213), that is an electrically conductive fluid, which is used to cool a portion of a body lumen BL within which the ultrasound transducer 511 may be positioned. Examples of types of electrically conductive cooling fluids that can be used were described above with reference to the embodiments of FIGS. 4A-4D, and thus, need not be repeated. The electrical insulator 504 can be made of parylene, or any of the other types of electrical insulator materials or combinations thereof that were described above with reference to the electrical insulator 404. In a specific embodiment, the peripheral surface of the inner electrode 202 is covered by a parylene coating, and the opposing longitudinal ends of the inner electrode 202 are covered by an epoxy resin. Other combinations of the aforementioned electrical insulator materials are also possible and within the scope of the embodiments described herein.

Figure 6A:
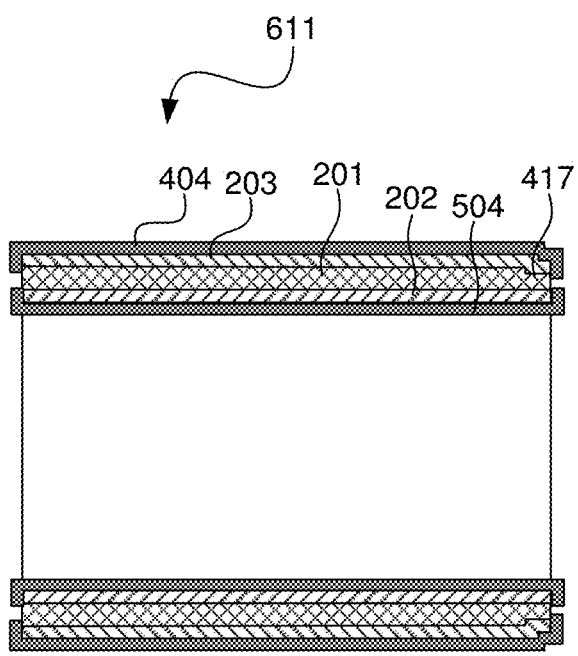
FIG. 6A illustrates a longitudinal cross-sectional view of a transducer, wherein both the inner and the electrodes of the piezoelectric transducer are covered by electrical insulators.
Figure 6B:
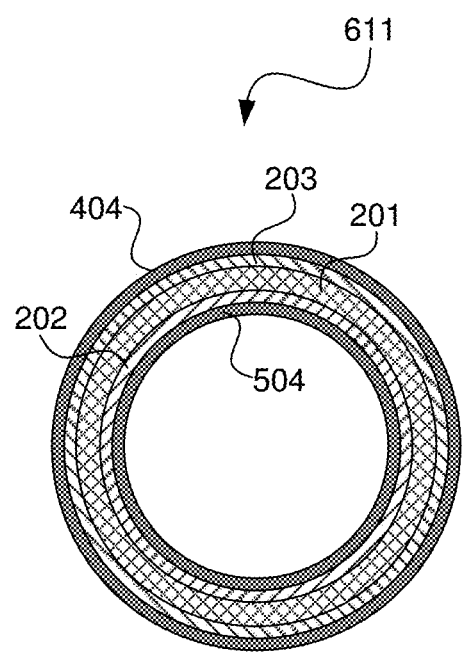
FIG. 6B illustrates a radial cross-sectional view of the transducer introduced in FIG. 6A, wherein both the inner and the electrodes of the piezoelectric transducer are covered by electrical insulators.

FIGS. 6A and 6B illustrate, respectively a longitudinal cross-sectional view and a radial-cross sectional view, of a transducer 611 where both the inner and outer electrodes 202, 203 of the piezoelectric transducer body 211 are covered by electrical insulators. More specifically, the inner electrode 202 is covered by the electrical insulator 504, and the outer electrode 203 is covered by the electrical insulator 404. As will be described in further detail below with reference to FIG. 7, insulating both the inner and outer electrodes 202, 203 (or more generally, both electrodes) of an ultrasound transducer provides for inferior performance, especially where an input electrical power is in the range of about 5 to 80 Watts, and an acoustic output power is in the range of about 5 to 45 Watts.

The selectively insulated transducers described above with reference to FIGS. 4A-4D, 5A and 5B, each of which includes a piezoelectric transducer body 201 comprising a hollow tube of piezoelectric material, can also include a backing member (e.g., 218), an isolation tube (e.g., 219), a standoff assembly (e.g., 230), and/or attachment points (334), examples of which were shown in and described above with reference to FIGS. 2C and 3B. However, to simplify the figures, these addition details were not shown in 4A-4D, 5A and 5B.

Figure 7:
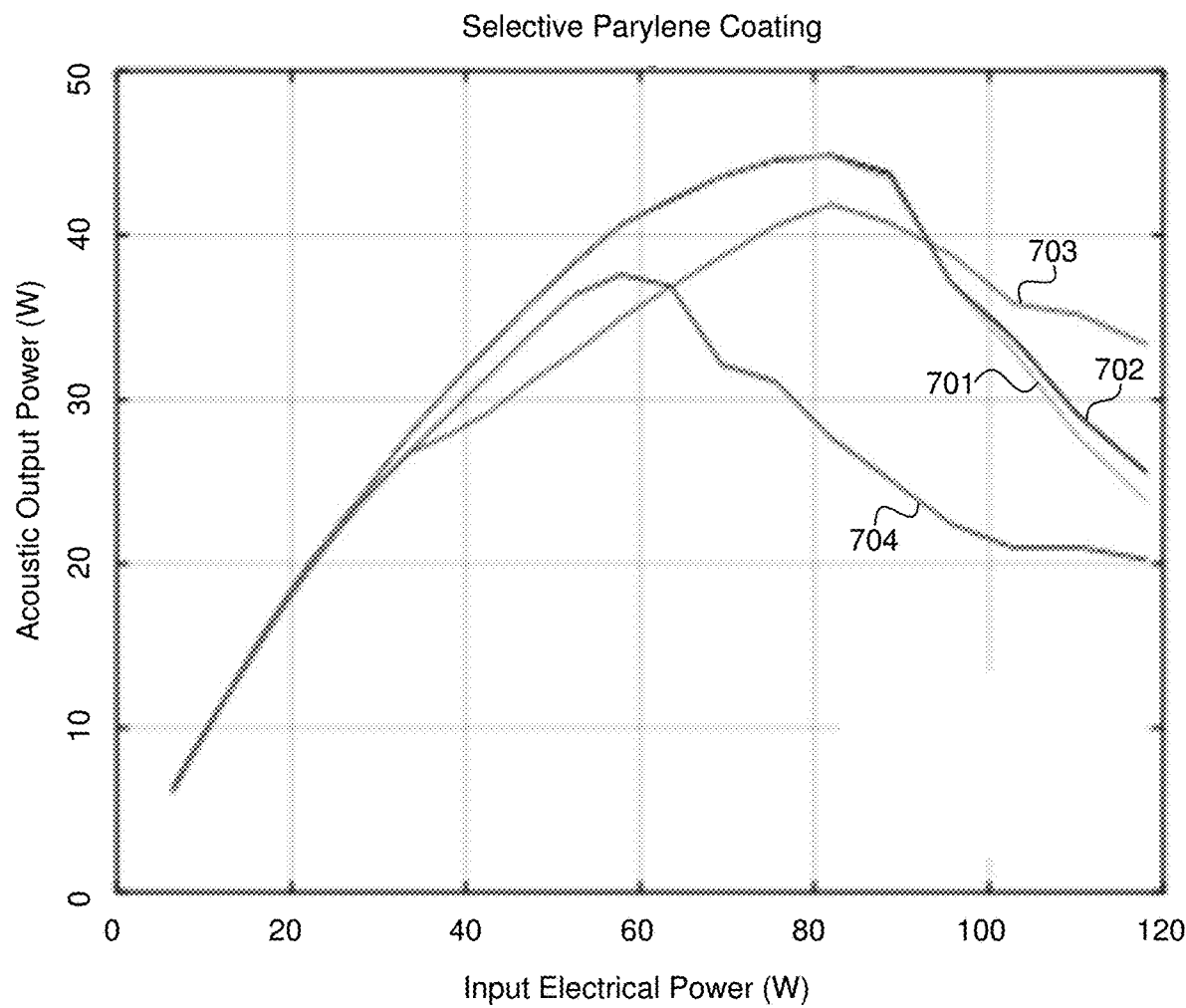
FIG. 7 is a graph of input electrical power versus acoustic output electrical power for a piezoelectric transducer showing how insulating various different electrodes or combinations thereof affect the performance of the transducer.

FIG. 7 is a graph of input electrical power versus acoustic output electrical power for a piezoelectric ultrasound transducer showing how insulating various different electrodes or combinations thereof may affect the performance of the ultrasound transducer submersed in a cooling fluid, wherein the piezoelectric transducer body 201 comprises a hollow tube of piezoelectric material having inner and outer surfaces on which inner and outer electrodes 202, 203 are respectively disposed. A radiation force balance (RFB), or some other instrument and technique, can be used to measure the acoustic output power of an ultrasound transducer in response to different electrical input powers. Referring to FIG. 7, the curve 701 corresponds to an ultrasound transducer (e.g., 111 in FIG. 2B) wherein both the inner and outer electrodes 202, 203 are not covered by an electrical insulator. As can be appreciated from the curve 701, the acoustic output power increases in response to increases in the input electrical power until the electrical input power reaches about 80 Watts (W), after which point the ultrasound transducer begins to break down and the acoustical output power rapidly declines. The curve 702 corresponds to an ultrasound transducer (e.g., 411) where the outer electrode 203 is covered by an electrical insulator (e.g., 404), but the inner electrode 202 is not covered by an electrical insulator. As can be appreciated from FIG. 7, the curves 701 and 702 are almost identical. Accordingly, in the curve 702, the acoustic output power increases in response to increases in the input electrical power until the electrical input power reaches about 80 W, after which point the ultrasound transducer begins to break down and the acoustical output power rapidly declines.

The curve 703 corresponds to an ultrasound transducer (e.g., 511) where the inner electrode 202 is covered by an electrical insulator (e.g., 504), but the outer electrode 203 is not covered by an electrical insulator. As can be appreciated from FIG. 7, while the efficiency of the ultrasound transducer (e.g., 511) is somewhat less than those where neither of the electrodes 202, 203 is covered by an electrical insulator, or where only the outer electrode 203 is covered by an electrical insulator, the acoustic output power still increases in response to increases in the input electrical power until the electrical input power reaches about 80 W, after which point the ultrasound transducer begins to break down and the acoustical output power rapidly declines. The curve 704 corresponds to an ultrasound transducer (e.g., 611) where both the inner electrode 202 is covered by an electrical insulator (e.g., 504) and the outer electrode 203 is covered by an electrical insulator (e.g., 404). As can be appreciated from the curve 704, the acoustic output power increases in response to increases in the input electrical power until the electrical input power reaches about 58 W, after which point the ultrasound transducer begins to break down and the acoustical output power rapidly declines. The electrical insulators (e.g., 404 and 504) tested to produce the curves 702, 703, and 704 were parylene C coatings.

When performing the experiments that produced the graph shown in FIG. 7, the cooling fluid (in which the tested transducers were submersed) was deionized water, which is a non-electrically conductive fluid. The reason that a non-electrically conductive fluid was used for such experiments was that, if an electrically conductive cooling fluid were used, then an electrical short would have occurred between the uninsulated electrodes of the ultrasound transducer (e.g., 111) whose performance is represented by the curve 701. With respect to the selectively insulated ultrasound transducers (e.g., 411 and 511) whose performances are represented by the curves 702 and 703, and with respect to the transducer (e.g., 611) having both its electrodes covered by electrical insulators whose performance is represented in the curve 704, it is believed that the curves 702, 703, and 704 in FIG. 7 also respectively show how such transducers would perform if submersed in an electrically conductive cooling fluid, such as saline, sodium lactate solution, or blood.

As can be appreciated from FIG. 7, the selectively insulated transducer that provided the best performance was the selectively insulated transducer (e.g., 411) where only the outer electrode 203 was covered by the parylene coating type of electrical insulator for input electrical powers under about 90 W (as shown by the curve 702), with the next best performance provided by the selectively insulated transducer (e.g., 511) where only the inner electrode 202 was covered by the parylene coating type of electrical insulator (as shown by the curve 703). As can also be appreciated from FIG. 7, the transducer (e.g., 611) where both the inner and outer electrodes 202, 203 were coated by the parylene coating type of electrical insulator breaks down at a significantly lower input electrical power (as shown by the curve 704), and thus, provides for inferior performance.

More specifically, from FIG. 7, it can be understood that covering both the inner and outer electrodes 202, 203 with respective electrical insulators degrades the transducer's power performance (curve 704) at higher input powers, e.g., at input powers above around 30 W, at which the transducer's ultrasonic output power is lower than it would have been without any electrical insulator (curve 701), or than it would have been with only one of the electrodes covered with an electrical insulator (curves 702 and 703). Without wishing to be bound by any theory, it is believed that such degradation may result from thermally induced mechanical stress in the transducer during its operation at higher power levels, for example, because electrical insulators on both electrodes of the piezoelectric transducer body 201 may trap heat within that piezoelectric material, causing mechanical stress. From FIG. 7, it also may be understood that covering just the inner electrode 202 with the electrical insulator may also degrade the transducer's acoustic output power performance (curve 703) at higher input powers, e.g., at input powers above around 30 W, at which the transducer's acoustic output power is lower than it would have been without the electrical insulator. In comparison, the power performance (curve 702) of a selectively insulated transducer having only the outer electrode 203 covered with the electrical insulator, such as described with reference to FIGS. 4A-4D, may be similar at all powers to the power performance (curve 701) of an uninsulated ultrasonic transducer. Nonetheless, it is expressly contemplated that in some configurations and implementations, it may be suitable to cover only the inner electrode 202 with an electrical insulator. It should be appreciated that operations of methods, described with reference to FIG. 11, suitably may be modified based on the particular arrangement of electrical insulator of the selectively insulated transducer.

In certain embodiments suitable, e.g., for renal denervation, the preferred range of electrical input power may be from about 30 W to about 50 W, corresponding to an acoustic output power of about 25 W to about 35 W. As seen in FIG. 7, coating both the inner electrode 202 and the outer electrode 203 (curve 704) reduces the efficiency of the transducer at these power input ranges compared to an uninsulated transducer (curve 701) or transducer where only outer electrode 203 is coated (curve 702). Without prejudice or limitation, it is theorized that coating both inner and outer electrodes 202, 203 (or more generally, both electrodes) of a transducer 111 may detrimentally affect the lifecycle of a transducer itself by generating more heat and mechanical stress on a catheter (e.g., 102) than transducers having uninsulated electrodes or transducers with only the outer electrode 203 is insulated (or only the inner electrode 202 is insulated).

As seen in FIG. 7, covering only the inner electrode 202 with an electrical insulator (curve 703) reduces the efficiency of transducer at power input ranges of between about 30 W to about 50 W compared to an uninsulated transducer (curve 701), or compared to a transducer where only the outer electrode 203 is covered with an electrical insulator (curve 702). Further, it is theorized that covering only inner electrode 202 with an electrical insulator (e.g., 504) may also detrimentally affect the lifecycle of a transducer by generating more heat and mechanical stress than a transducer having uninsulated electrodes or a transducer with only the outer electrode 203 is covered with an electrical insulator (e.g., 404). This may be because a cooling fluid (e.g., 213) inserted into a balloon (or blood in a balloonless embodiment) may only come into contact with the electrical insulator (e.g., 504) covering the inner electrode 202 via openings (e.g., 336) of stand-off assembly (e.g., 230), making it difficult for the cooling fluid to effectively pull heat away from inner electrode 202. By contrast, where a cooling fluid (e.g., 213) is fed into a balloon (or blood in a balloonless embodiment) may more fully come into contact with the electrical insulator (e.g., 404) covering an outer electrode 203 and therefore may more readily whisk away heat that might otherwise be trapped by the electrical insulator, e.g., a parylene coating, covering the outer electrode 203.

In the above described embodiments, the piezoelectric transducer body was shown and described has being made of a hollow tube of piezoelectric material and having inner and outer surfaces on which inner and outer electrodes are respectively disposed. In alternative embodiments the piezoelectric transducer body need not be hollow. For an example, as shown in FIGS. 8A and 8B, an ultrasound transducer 811 can include a piezoelectric transducer body 801 that is generally rectangular with first and second planar opposing surfaces (i.e., top and bottom surface in this example) that are parallel to one another, on which are disposed electrodes 802 and 803 that planar and parallel to one another. For the sake of this discussion, the electrodes 802 and 803 will be referred to, respectively, as the lower and upper electrodes. Referring to FIG. 9, in accordance with certain embodiments, a selectively insulated ultrasound transducer 911 has a generally rectangular piezoelectric transducer body 801 with only the upper electrode 803 covered by an electrical insulator 904. In such embodiments the electrical insulator 904 provides for both electrical isolation and physical isolation of the upper electrode 803 from an electrically conductive fluid that the transducer is placed within. Referring to FIG. 10, in accordance with certain embodiments, an ultrasound transducer 1011 has a generally rectangular piezoelectric transducer body 801 with only the lower electrode 802 covered by an electrical insulator 1004. In such embodiments the electrical insulator 1004 provides for both electrical isolation and physical isolation of the lower electrode 802 from an electrically conductive fluid that the transducer is placed within.

In certain embodiments, each of the selectively insulated ultrasound transducers 911, 1011 can be placed within a balloon (e.g., 112) that is at least partially filled with a cooling fluid (e.g., 213), that is an electrically conductive fluid, which is used to cool a portion of a body lumen BL within which the ultrasound transducers may be positioned. As noted above, the electrically conductive fluid can also cool the ultrasound transducer itself. Examples of types of electrically conductive cooling fluids that can be used were described above with reference to the embodiments of FIGS. 4A-4D, and thus, need not be repeated. In alternative embodiments, which can be referred to as balloonless embodiments, the selectively insulated ultrasound transducers 911 or 1011 can be directly exposed to blood flowing through a body lumen within which the ultrasound transducers may be positioned, in which case the electrically conductive fluid comprises the blood.

The electrical insulators 904 and 1004 can be made of parylene, or any of the other types of materials or combinations thereof that were described above with reference to the electrical insulator 404. In a specific embodiment, the peripheral surface of one of the outer electrode 803 (or 802) is covered by a parylene coating, and the opposing longitudinal ends of the one of the electrode 803 (or 802) are covered by an epoxy resin. Other combinations of the aforementioned electrical insulator materials are also possible and within the scope of the embodiments described herein.

Embodiments of the present technology are not limited to ultrasound transducers having the specific shapes shown in the FIGS. and described above. For an example, a cylindrical (or other shaped) hollow piezoelectric transducer body need not have a constant outer diameter, but rather, may have longitudinal distal and/or proximal ends that are stepped, or more specifically, that have a smaller diameter that the remainder (i.e., the non-stepped portion) of the transducer body. Other variations are also possible and within the scope of the embodiments described herein. the non-stepped portion of the transducer body can comprise a vast majority of the transducer length, such as, for example, 50-95% or 60-90% (e.g., 50-60%, 60-70%, 70-80%, 80-90%, 90-95%, 90-99%, percentages between the foregoing ranges, etc.) of the overall length of the transducer. In other embodiments, however, non-stepped portion can extend along less than 60% (e.g., 40-50%, 50-55%, 55-60%, less than 40%, etc.) or greater than 95% (e.g., 95-96, 96-97, 97-98, 98-99%, more than 99%, etc.) of the overall length of the transducer, as desired or required.

Further, it is noted that where the piezoelectric transducer body is not hollow, such as in the embodiments described with reference to FIGS. 8A-10, the shape of the piezoelectric transducer body can have other shapes besides being generally rectangular with parallel upper and lower surfaces. For example, referring back to FIG. 8A-10, one or more of the upper and lower surfaces of the piezoelectric transducer body 801 shown therein can be concave or convex, or have some other nonplanar shape, thus resulting in one or more of the lower and upper electrodes 802, 803 have such alternative shapes. If one of such electrodes were coated with an electrical insulator, the electrical insulator would also have such alternative shapes.

Additional options regarding designs and uses of ultrasound transducers and catheter-based ultrasound delivery systems are provided in the following patents and published applications, the entire contents of each of which are incorporated by reference herein: U.S. Pat. Nos. 6,635,054; 6,763,722; 7,540,846; 7,837,676; 9,707,034; 9,981,108; 10,350,440; 10,456,605; 10,499,937; and PCT Publication No. WO 2012/112165.

The transducers, apparatuses, and systems described herein may be used to treat any suitable tissue, which tissue may be referred to as a target anatomical structure. For example, use of the present systems to treat (e.g., neuromodulate) the renal nerve is described above. It should be appreciated that body lumens, in which the present systems may be positioned for treating tissue, are not necessarily limited to naturally occurring body lumens. For example, the treatment may include creating a body lumen within tissue (e.g., using drilling, a cannula, laser ablation, or the like) and then positioning suitable components within such a body lumen. Other suitable applications for the present system include ablation of pulmonary nerve and tissue responsible veins or cardiac arrhythmia, nerves within that intervertebral disk, nerves within or outside of that intervertebral disk, basivertebral nerves within that vertebral bone, nerves within the brain tissue, tissue responsible for cardiac arrhythmia within the cardiac tissue, nerves along the bronchial tree, one or more esophageal branches of the vagus nerve, and one or more nerves surrounding the bladder.

Figure 11:
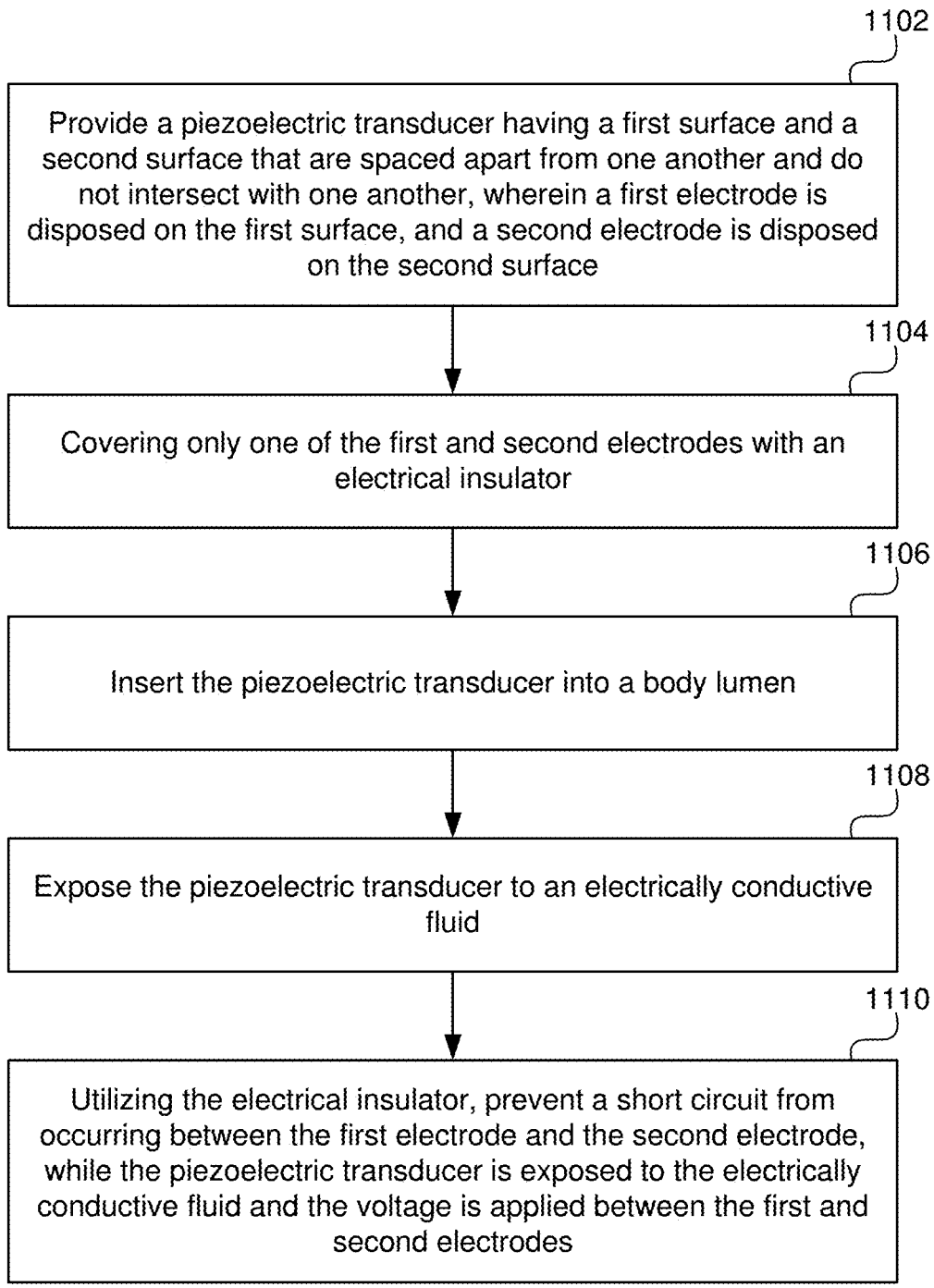
FIG. 11 is a high level flow diagram that is used to summarize methods according to various embodiments of the present technology.

FIG. 11 is a high level flow diagram that is used to summarize methods according to various embodiments of the present technology. Referring to FIG. 11, step 1102 involves providing a piezoelectric transducer having a first surface and a second surface that are spaced apart from one another and do not intersect with one another, wherein a first electrode is disposed on the first surface, and a second electrode is disposed on the second surface. Step 1104 involves covering only one of the first and second electrodes with an electrical insulator. Step 1106 involves inserting the piezoelectric transducer into a body lumen (e.g., a renal artery), and step 1108 involves exposing the piezoelectric transducer to an electrically conductive fluid that comes into contact with the second electrode, and that is inhibited (by the electrical insulator that covers the first electrode) from coming into contact with the first electrode. Step 1110 involves, while the piezoelectric transducer is exposed to the electrically conductive fluid (and inserted into a body lumen BL), applying a voltage between the first and second electrodes to thereby cause the piezoelectric transducer to produce ultrasonic waves. Step 1112 involves, utilizing the electrical insulator, inhibiting (and preferably preventing) a short circuit from occurring between the first electrode and the second electrode, while the piezoelectric transducer is exposed to the electrically conductive fluid and the voltage is applied between the first and second electrodes.

In certain embodiments, the method also includes placing the piezoelectric transducer inside of a balloon. In such an embodiment, exposing the piezoelectric transducer to the electrically conductive fluid, at step 1108, involves at least partially filling the balloon with the electrically conductive fluid. As explained above, the electrically conductive fluid can comprise at least one of saline, non-pure water, or sodium lactate solution, but is not limited thereto. In such embodiments, the method can also include inserting the balloon, with the piezoelectric transducer therein, into a body lumen. In such an embodiment, applying the voltage between the first and second electrodes to thereby cause the piezoelectric transducer to produce ultrasonic waves occurs while the balloon is within the body lumen.

In other embodiments, referred to herein as balloonless embodiments, step 1108 is performed by inserting the piezoelectric transducer into a body lumen through which blood is flowing such that the piezoelectric transducer comes into contact with the blood. In such embodiments, the electrically conductive fluid comprises the blood, and exposing the piezoelectric transducer to the electrically conductive fluid at step 208 comprises exposing the piezoelectric transducer to the blood.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited.

What is claimed is:

1. A catheter, comprising:
an ultrasound transducer disposed at a distal end of the catheter comprising a piezoelectric transducer body having a first surface and a second surface that are spaced apart from one another and do not intersect with one another;
a first electrode disposed on the first surface;
a second electrode disposed on the second surface;
an electrical insulator covering the first electrode and configured to inhibit the first electrode from coming into contact with an electrically conductive fluid when the ultrasound transducer is placed within the electrically conductive fluid,
wherein the second electrode is not covered by an electrical insulator;
wherein the catheter is configured such that the electrically conductive fluid comes into contact with the second electrode and the electrical insulator covering the first electrode when the ultrasound transducer is placed within the electrically conductive fluid;
wherein the ultrasound transducer is configured to be placed within a balloon that is at least partially filled with the electrically conductive fluid that is used to cool a portion of a body lumen within which the ultrasound transducer may be positioned; and
the electrically conductive fluid, that the balloon is at least partially filled with, comprises at least one of saline, non-pure water, or sodium lactate solution;
further comprising a backing member disposed within the ultrasound transducer, the backing member extending from a proximal end to a distal end of the ultrasound transducer and defining an interior lumen; and
one or more stand-off assemblies extending from the backing member, the one or more stand-off assemblies configured to engage the second electrode;
wherein the one or more stand-off assemblies define a plurality of openings defining an internal space between the backing member and the second electrode, the internal space being in fluid communication with an interior of the balloon via the plurality of openings so that, when in use, fluid entering the balloon passes along the first electrode and into the internal space between the backing member and the second electrode through the plurality of openings to transfer heat away from the ultrasound transducer, wherein the backing member and the one or more stand-off assemblies are coated with one or more electrical insulator materials.

2. The catheter of claim 1, wherein:
the piezoelectric transducer body is configured to generate ultrasonic waves in response to application of a voltage between the first and second electrodes; and
the electrical insulator that covers the first electrode inhibits a short circuit from occurring between the first electrode and the second electrode when the ultrasound transducer is placed within the electrically conductive fluid and the voltage is applied between the first and second electrodes.

3. The catheter of claim 1, wherein:
the piezoelectric transducer body comprises a hollow tube of piezoelectric material having an inner surface and an outer surface, the inner surface being one of the first and second surfaces of the piezoelectric transducer body, and the outer surface being the other one of the first and second surfaces of the piezoelectric transducer body;
the first electrode is disposed on one of the inner and outer surfaces of the hollow tube of piezoelectric material; and
the second electrode is disposed on the other one of the inner and outer surfaces of the hollow tube of piezoelectric material.

4. The catheter of claim 3, wherein:
the first electrode is disposed on the outer surface of the hollow tube of piezoelectric material;
the second electrode is disposed on the inner surface of the hollow tube of piezoelectric material;
the electrical insulator covers the first electrode, which is disposed on the outer surface of the hollow tube of piezoelectric material; and
the second electrode, which is disposed on the inner surface of the hollow tube of piezoelectric material, is not covered by an electrical insulator.

5. The catheter of claim 4, wherein:
the hollow tube of piezoelectric material is cylindrically shaped.

6. The catheter of claim 1, wherein the piezoelectric transducer body is configured to deliver acoustic energy in a frequency range of 8.5 to 9.5 MHz.

7. The catheter of claim 1, wherein the piezoelectric transducer body is configured to produce an acoustic output power within a range of 5 to 45 Watts in response to an input electrical power within a range of 10 to 80 Watts.

8. The catheter of claim 1, wherein:
the first electrode includes a major peripheral surface and longitudinal ends;
a portion of the electrical insulator, which covers the major peripheral surface of the first electrode, is made of a first type of electrically insulating material; and
a further portion of the electrical insulator, which covers the longitudinal ends of the first electrode, is made of a same material or a different material than the electrically insulating material that covers the major peripheral surface of the first electrode.

9. The catheter of claim 1, wherein the electrical insulator comprises parylene.

10. The catheter of claim 1, wherein the electrical insulator comprises one or more of the following:
parylene;
cyanoacetate;
epoxy resin;
nylon;
polytetrafluoroethylene (PTFE);
polyimide;
polyethylene;
polyethylene terephthalate;
polyvinyl chloride (PVC); and
synthetic diamond coating.

11. The catheter of claim 1, wherein the electrical insulator comprises parylene disposed on and covering an outer circumference of the first electrode and an epoxy resin disposed on and covering longitudinal ends of the first electrode.

12. An apparatus, comprising:
a balloon configured to receive a cooling fluid; and
an ultrasound transducer disposed within the balloon;
the ultrasound transducer comprising a hollow tube of piezoelectric material having an inner surface and an outer surface, a first electrode disposed on one of the inner or outer surfaces of the hollow tube of piezoelectric material, a second electrode disposed on the other one of the inner or outer surfaces of the hollow tube of piezoelectric material, and an electrical insulator coating the first electrode and configured to inhibit the first electrode from coming into contact with the cooling fluid received by the balloon, and thereby inhibit electrical conduction between the first electrode and the second electrode when the cooling fluid received by the balloon is an electrically conductive cooling fluid, wherein the second electrode is not covered by an electrical insulator, and wherein the apparatus is configured such that the electrically conductive fluid comes into contact with the second electrode and the electrical insulator covering the first electrode when the ultrasound transducer is placed within the electrically conductive fluid;

further comprising a backing member disposed within the ultrasound transducer, the backing member extending from a proximal end to a distal end of the ultrasound transducer and defining an interior lumen; and one or more stand-off assemblies extending from the backing member, the one or more stand-off assemblies configured to engage the second electrode;

wherein the one or more stand-off assemblies define a plurality of openings defining an internal space between the backing member and the second electrode, the internal space being in fluid communication with an interior of the balloon via the plurality of openings so that, when in use, fluid entering the balloon passes along the first electrode and into the internal space between the backing member and the second electrode through the plurality of openings to transfer heat away from the ultrasound transducer, wherein the backing member and the one or more stand-off assemblies are coated with one or more electrical insulator materials.

13. The apparatus of claim 12, wherein:
the ultrasound transducer is configured to generate ultrasonic waves in response to application of a voltage between the first and second electrodes; and
wherein the electrical insulator covering the first electrode inhibits a short circuit from occurring between the first electrode and the second electrode when the cooling fluid received within the balloon is an electrically conductive cooling fluid and the voltage is applied between the first and second electrodes.

14. The apparatus of claim 12, wherein the electrical insulator comprises at least one of the following:
parylene;
cyanoacetate;
epoxy resin;
nylon;
polytetrafluoroethylene (PTFE);
polyimide;
polyethylene;
polyethylene terephthalate;
polyvinyl chloride (PVC); and
synthetic diamond coating.

15. The apparatus of claim 14, wherein the first electrode, which is covered by the electrical insulator, is disposed on the outer surface of the hollow tube of piezoelectric material.

16. The apparatus of claim 12, wherein:
the electrically conductive fluid comprises at least one of saline, non-pure water, or sodium lactate solution.

17. The apparatus of claim 12, wherein the hollow tube of piezoelectric material is cylindrically shaped.

18. A method for treating a body lumen in a mammal, comprising:
providing an ultrasound transducer having a first surface and a second surface that are spaced apart from one another and do not intersect with one another, wherein a first electrode is disposed on the first surface, and a second electrode is disposed on the second surface;
further providing a backing member disposed within the ultrasound transducer, the backing member extending from a proximal end to a distal end of the ultrasound transducer and defining an interior lumen; and one or more stand-off assemblies extending from the backing member, the one or more stand-off assemblies configured to engage the second electrode, wherein the backing member and the one or more stand-off assemblies are coated with one or more electrical insulator materials;
covering only the first electrode with an electrical insulator;
placing the ultrasound transducer inside of a balloon;
exposing the ultrasound transducer to an electrically conductive fluid that comes into contact with the second electrode and the electrical insulator, and that is inhibited from coming into contact with the first electrode by the electrical insulator that covers the first electrode, wherein the exposing the ultrasound transducer to the electrically conductive fluid comprises at least partially filling the balloon with the electrically conductive fluid, wherein the one or more stand-off assemblies define a plurality of openings defining an internal space between the backing member and the second electrode, the internal space being in fluid communication with an interior of the balloon via the plurality of openings so that, during the exposing, fluid entering the balloon passes along the first electrode and into the internal space between the backing member and the second electrode through the plurality of openings to transfer heat away from the ultrasound transducer;
while the ultrasound transducer is exposed to the electrically conductive fluid, applying a voltage between the first and second electrodes to thereby cause the ultrasound transducer to produce ultrasonic waves; and
utilizing the electrical insulator, inhibiting a short circuit from occurring between the first electrode and the second electrode, while the ultrasound transducer is exposed to the electrically conductive fluid and the voltage is applied between the first and second electrodes.

19. The method of claim 18, further comprising:
inserting the balloon, with the ultrasound transducer therein, into a body lumen;
wherein the applying the voltage between the first and second electrodes to thereby cause the ultrasound transducer to produce ultrasonic waves occurs while the balloon is within the body lumen.

20. The method of claim 18, further comprising providing the electrically conductive fluid, during the exposing, wherein the electrically conductive fluid comprises at least one of saline, non-pure water, or sodium lactate solution.

21. The method of claim 18, where the body lumen is a blood vessel through which blood is flowing, further comprising:
inserting the ultrasound transducer into the body lumen such that the electrically conductive fluid is the blood;
wherein the exposing the ultrasound transducer to the electrically conductive fluid comprises exposing the ultrasound transducer to the blood.

22. The catheter of claim 1,
wherein each of the first electrode and the second electrode comprise a plurality of electrically conductive layers, and wherein each layer comprises a material selected from the group consisting of: copper, silver, gold, and nickel.

23. The apparatus of claim 12, further comprising:
a cable contacting the first electrode and configured to provide power to the first electrode;
wherein the electrical insulator covers both a peripheral surface of the first electrode and a contact between the cable and the first electrode.

24. The ultrasound transducer of claim 22, wherein the first electrode and the second electrode have the same thickness.

25. The ultrasound transducer of claim 22, wherein each of the first electrode and the second electrode are made of the same electrically conductive layers.

26. The ultrasound transducer of claim 22, wherein at least one of the first electrode and the second electrode comprises a first layer comprising copper, the first layer in contact with the piezoelectric transducer body.

27. The ultrasound transducer of claim 26, wherein at least one of the first electrode and the second electrode comprises a second layer comprising nickel, the second layer in contact with the first layer.

28. The ultrasound transducer of claim 27, wherein at least one of the first electrode and the second electrode comprises a third layer comprising gold, the third layer in contact with the second layer.

29. The catheter of claim 1, wherein the first electrode comprises two opposing longitudinal ends; and wherein the two opposing longitudinal ends are covered by a second electrical insulator different from the electrical insulator covering the first electrode.

30. The catheter of claim 29, wherein the second electrical insulator is an epoxy resin.

31. The catheter of claim 1, wherein the first electrode comprises two opposing longitudinal ends; and wherein the two opposing longitudinal ends are covered by the electrical insulator covering the first electrode.

32. The catheter of claim 1, wherein the electrical insulator has a thickness between 10 μm to 20 μm.

\* \* \* \* \*